US012766093B2

(12) United States Patent
Dewar

(10) Patent No.: US 12,766,093 B2
(45) Date of Patent: *Oct. 20, 2026

(54) COLLOIDAL SILVER COMBINED WITH PLANT EXTRACTS FOR USE IN TREATING WOUNDS AND OTHER SKIN CONDITIONS

(71) Applicant: Phyto Sophos Ltd., London (GB)

(72) Inventor: Laura Dewar, Chislehurst (GB)

(73) Assignee: Phyto Sophos Ltd., London (GB)

( * ) Notice: Subject to any disclaimer, the term of this patent is extended or adjusted under 35 U.S.C. 154(b) by 188 days.

This patent is subject to a terminal disclaimer.

(21) Appl. No.: 18/897,153

(22) Filed: Sep. 26, 2024

(65) Prior Publication Data

US 2025/0009642 A1 Jan. 9, 2025

Related U.S. Application Data

(63) Continuation of application No. 16/499,406, filed as application No. PCT/GB2018/050869 on Mar. 29, 2018, now Pat. No. 12,128,128.

(30) Foreign Application Priority Data

Mar. 30, 2017 (GB) ..................................... 1705140

(51) Int. Cl.

| | |
|---|---|
| ***A61K 8/9789*** | (2017.01) |
| ***A61K 8/02*** | (2006.01) |
| ***A61K 8/19*** | (2006.01) |
| ***A61K 8/9794*** | (2017.01) |
| ***A61K 36/185*** | (2006.01) |
| ***A61K 36/74*** | (2006.01) |
| ***A61Q 19/00*** | (2006.01) |

(52) U.S. Cl.

CPC .......... *A61K 8/9789* (2017.08); *A61K 8/0208* (2013.01); *A61K 8/19* (2013.01); *A61K 8/9794* (2017.08); *A61K 36/185* (2013.01); *A61K 36/74* (2013.01); *A61Q 19/00* (2013.01)

(58) Field of Classification Search

CPC .... A61K 2300/00; A61K 33/38; A61K 36/11; A61K 36/185; A61K 36/258; A61K 36/28; A61K 36/30; A61K 36/38; A61K 36/48; A61K 36/66; A61K 36/74; A61K 36/886; A61K 8/0208; A61K 8/19; A61K 8/9789; A61K 8/9794; A61K 9/0014; A61K 36/14; A61K 36/25; A61K 36/29; A61K 36/36; A61K 36/70; A61K 8/97; A61K 8/9741; A61K 8/9755; A61K 8/9783; A61P 17/02; A61P 17/00; A61Q 19/00

See application file for complete search history.

(56) References Cited

U.S. PATENT DOCUMENTS

| | | | |
|---|---|---|---|
| 6,103,272 A | 8/2000 | Keeney | |
| 7,678,393 B1 | 3/2010 | Duncan et al. | |
| 12,128,128 B2 * | 10/2024 | Dewar ............... | A61K 2300/00 |
| 2004/0185123 A1 | 9/2004 | Mazzio et al. | |
| 2011/0262558 A1 | 10/2011 | Huckfeldt et al. | |

FOREIGN PATENT DOCUMENTS

| | | |
|---|---|---|
| DE | 102006049929 A1 | 4/2008 |
| DE | 202009014065 U1 | 2/2010 |
| DE | 202015006527 U1 | 12/2015 |
| JP | 2001/031580 A | 2/2001 |
| JP | 2003/005241 A | 2/2003 |
| JP | 2006/504799 A | 2/2003 |
| JP | 2005/194246 A | 7/2005 |
| JP | 2010/0132629 A | 6/2010 |
| JP | 2010/0540574 A | 12/2010 |
| JP | 2007/506685 A | 3/2022 |
| RU | 2432146 C1 | 10/2011 |
| WO | WO 2005/002608 A1 | 1/2005 |
| WO | WO 2005/120173 A2 | 12/2005 |
| WO | WO 2008/080980 A1 | 7/2008 |
| WO | WO 2016/070194 A1 | 5/2016 |
| WO | WO 2008/104076 A1 | 9/2018 |

OTHER PUBLICATIONS

International Search Report & Written Opinion, PCT Application No. PCT/GB2018/050869, dated Jul. 18, 2018, 17 pages.

* cited by examiner

*Primary Examiner* — Jeffrey T. Palenik

(74) *Attorney, Agent, or Firm* — Morgan, Lewis & Bockius LLP

(57) ABSTRACT

In one aspect, a composition for topical application is provided. The composition comprises a base. Dispersed within the base is elemental silver as a colloidal suspension, and plant extract from at least 6 plants. The plants are selected from the group consisting of *Echinacea purpurea, Stellaria media, Aloe vera, Matricaria recutita, Hypericum perforatum, Calendula officinalis, Equisetum arvense, Symphytum officinale, Panax ginseng, Rumex crispus, Arctium lappa, Trifolium pratense, Chelidonium majus, Thuja occidentalis, Urtica dioica, Mahonia aquifolium,* and *Galium aparine.*

15 Claims, 6 Drawing Sheets

COLLOIDAL SILVER COMBINED WITH PLANT EXTRACTS FOR USE IN TREATING WOUNDS AND OTHER SKIN CONDITIONS

CROSS-REFERENCE TO RELATED APPLICATIONS

This application is a continuation application of U.S. application Ser. No. 16/499,406, filed Sep. 30, 2019, which is a U.S. National Phase Application under 35 U.S.C. § 371 of International Application No. PCT/GB2018/050869, filed Mar. 29, 2018, which claims priority to, and the benefit of, United Kingdom Application No. 1705140.0, filed Mar. 30, 2017. The contents of each of these applications are incorporated herein by reference in their entireties.

TECHNICAL FIELD

The present invention relates to compositions for topical application. In particular, the present invention relates to compositions for topical application comprising colloidal silver and a combination of plant extracts, for use as cosmetics and/or medicaments.

BACKGROUND

There are a number of dermatological conditions and cosmetic skin conditions which may cause distress to humans or animals. Said distress may be due to sensations such as pain, itching, or burning. Said distress may alternatively or additionally be due to an unsightly appearance associated with the condition, such as reddening of the skin, dry skin, or pigmentation of the skin.

Sufferers presenting with these conditions often wish to alleviate their distress by using some form of remedy for the condition. One option for addressing these conditions may be the use of prescription or over-the-counter pharmaceutical preparations. However, there is a consumer demand for natural remedies, or non-pharmaceutical remedies.

Given that these conditions may affect only a portion of the surface of the body of a sufferer, there is a consumer demand for a local approach of addressing the dermatological condition or cosmetic skin condition, rather than a systemic approach. One such suitable approach may be a topical application of a remedy which may reduce or diminish the dermatological condition or cosmetic skin condition.

Accordingly, there is a need for compositions suitable for topical application to dermatological conditions and/or cosmetic skin conditions which may at least partially alleviate pain, itching, burning, reddening of the skin, dry skin, or pigmentation of the skin, as appropriate.

SUMMARY

According to a first aspect of the present invention, there is provided a composition for topical application comprising a base, and dispersed within the base:

elemental silver as a colloidal suspension; and plant extract from at least 6 plants selected from the group consisting of *Echinacea purpurea, Stellaria media, Aloe vera, Matricaria recutita, Hypericum perforatum, Calendula officinalis, Equisetum arvense, Symphytum officinale, Panax ginseng, Rumex crispus, Arctium lappa, Trifolium pratense, Chelidonium majus, Thuja occidentalis, Urtica dioica, Mahonia aquifolium,* and *Galium aparine.*

According to further aspects, there is provided:

2) A composition according to 1), wherein the composition comprises:

base in an amount of from 80% to 99.9% by volume/volume of the composition;

elemental silver in an amount of from 1×10−5% to 1×10−2% by weight/volume of the composition; and plant extract in an amount of from 0.1% to 10% by weight/volume of the composition.

3) A composition according to 1) or 2), wherein the composition is an aqueous suspension, a cream, an ointment, a spray, a gel, or an aerosol.

4) A composition according to 3), wherein the composition is an aqueous suspension, and the base is water.

5) A composition according to 4), wherein the composition consists essentially of:

elemental silver in an amount of from 1×10−5% to 1×10−2% by weight/volume of the composition;

plant extract in an amount of from 0.1% to 10% by weight/volume of the composition; and water as the remainder of the composition up to 100%.

6) A composition according to any of 1) to 5), wherein the plant extract is an extract in an extractant selected from Ci-C4 alkanol, acetic acid, glycerine, propylene glycol, honey, water, and mixtures thereof.

7) A composition according to 6), wherein the extractant consists of aqueous ethanol.

8) A composition according to 6) or 7), wherein the plant extract is an extract of plant material in a ratio of from 1:1 to 1:12 weight/volume of plant material to extractant.

9) A composition according to any of 1) to 5), wherein the extract is an extractant-free extract.

10) A composition according to any of 1) to 9), wherein the plant extracts are from *Equisetum arvense, Rumex crispus, Arctium lappa, Trifolium pratense, Chelidonium majus, Thuja occidentalis, Urtica dioica, Symphytum officinale, Mahonia aquifolium, Echinacea purpurea, Stellaria media, Galium aparine, Aloe vera, Matricaria recutita, Hypericum perforatum, Calendula officinalis,* and *Panax ginseng.*

11) A composition according to any of 1) to 9), wherein the plant extracts are from *Equisetum arvense, Symphytum officinale, Echinacea purpurea, Stellaria media, Aloe vera, Matricaria recutita, Hypericum perforatum, Calendula officinalis,* and *Panax ginseng.*

12) A composition according to any of 1) to 9), wherein the plant extracts are from *Symphytum officinale, Echinacea purpurea, Aloe vera, Matricaria recutita, Hypericum perforatum, Calendula officinalis,* and *Panax ginseng.*

13) A composition according to any of 1) to 9), wherein the plant extracts are from *Galium aparine, Aloe vera, Matricaria recutita, Hypericum perforatum, Calendula officinalis,* and *Panax ginseng.*

14) A composition according to any of 1) to 9), wherein the plant extracts are from *Chelidonium majus, Thuja occidentalis, Echinacea purpurea, Galium aparine, Matricaria recutita, Hypericum perforatum,* and *Calendula officinalis.*

15) A composition according to any of 1) to 9), wherein the plant extracts are from *Equisetum arvense, Symphytum officinale, Mahonia aquifolium, Matricaria recutita, Hypericum perforatum, Calendula officinalis,* and *Panax ginseng.*

16) A composition according to any of 1) to 9), wherein the plant extracts are from *Arctium lappa, Echinacea*

*purpurea, Stellaria media, Matricaria recutita, Hypericum perforatum,* and *Calendula officinalis.*

17) A composition according to any of 1) to 9), wherein the plant extracts are from *Chelidonium majus, Thuja occidentalis, Mahonia aquifolium, Aloe vera, Matricaria recutita,* and *Calendula officinalis.*

18) A composition according to any of 1) to 9), wherein the plant extracts are from *Arctium lappa, Urtica dioica, Echinacea purpurea, Stellaria media, Matricaria recutita, Hypericum perforatum,* and *Calendula officinalis.*

19) A composition according to any of 1) to 9), wherein the plant extracts are from *Urtica dioica, Symphytum officinale, Echinacea purpurea, Stellaria media, Aloe vera, Matricaria recutita,* and *Calendula officinalis.*

20) A composition according to any of 1) to 9), wherein the plant extracts are from *Urtica dioica, Symphytum officinale, Mahonia aquifolium, Echinacea purpurea, Stellaria media, Aloe vera, Matricaria recutita, Hypericum perforatum, Calendula officinalis,* and *Panax ginseng.*

21) A composition according to any of 1) to 9), wherein the plant extracts are from *Rumex crispus, Arctium lappa, Trifolium pratense, Symphytum officinale, Echinacea purpurea, Stellaria media, Hypericum perforatum, Calendula officinalis,* and *Panax ginseng.*

22) A composition according to any of 1) to 9), wherein the plant extracts are from *Urtica dioica, Symphytum officinale, Echinacea purpurea, Stellaria media, Aloe vera, Matricaria recutita,* and *Calendula officinalis.*

23) A composition according to any of 1) to 9), wherein the plant extracts are from *Rumex crispus, Arctium lappa, Trifolium pratense, Symphytum officinale, Echinacea purpurea, Stellaria media, Matricaria recutita,* and *Calendula officinalis.*

24) A composition according to any of 1) to 23) which is a cosmetic composition.

25) A composition according to any of 1) to 23) for use as a medicament.

26) A composition according to any of 1) to 10) for use in the treatment of dermatitis.

27) A composition according to any of 1) to 9) or 11) for use in the treatment of severed skin.

28) A composition according to any of 1) to 9) or 12) for use in the treatment of burns.

29) A composition according to any of 1) to 9) or 13) for use in the treatment of sunburn.

30) A composition according to any of 1) to 9) or 14) for use in the treatment of Tinea pedis.

31) A composition according to any of 1) to 9) or 15) for use in the treatment of blisters.

32) A composition according to any of 1) to 9) or 18) for use in the treatment of insect bites.

33) A composition according to any of 1) to 9) or 19) for use in the treatment of irritant diaper dermatitis.

34) A composition according to any of 1) to 9) or 20) for use in the treatment of contact dermatitis related to incontinence.

35) A method of manufacturing a composition for topical application, the method comprising:

providing plant extract from at least 6 plants selected from the group consisting of *Equisetum arvense, Rumex crispus, Arctium lappa, Trifolium pratense, Chelidonium majus, Thuja occidentalis, Urtica dioica, Symphytum officinale, Mahonia aquifolium, Echinacea purpurea, Stellaria media, Galium aparine, Aloe vera, Matricaria recutita, Hypericum perforatum, Calendula officinalis,* and *Panax ginseng;* providing a colloidal suspension of elemental silver in a base, the elemental silver content of the colloidal suspension being of from 1×10−5% to 1×10−2% by weight/volume of the base; and combining the plant extract and the colloidal suspension of elemental silver to provide a composition for topical application.

36) A method according to 35), wherein the base is water.

37) A method according to 35) or 36), wherein the plant extract and colloidal suspension of elemental silver are combined in a ratio of from 1:20 to 1:4 weight/volume plant extract to colloidal suspension of elemental silver.

38 A dressing comprising a composition according to any of 1) to 34).

39) A porous sheet impregnated with a composition according to any of 1) to 34).

40) A method of treating an area affected by a dermatological condition comprising:

providing a composition according to any of 1) to 34); and topically applying the composition to the area affected by the dermatological condition.

41) A non-therapeutic cosmetic method comprising:

providing a composition according to any of 1) to 34);

selecting an area of the body to which the composition should be applied; and topically applying the composition to the selected area.

Further features and advantages of the invention will become apparent from the following description of preferred embodiments of the invention, given by way of example only, which is made with reference to the accompanying drawings.

DETAILED DESCRIPTION

Figure 1:
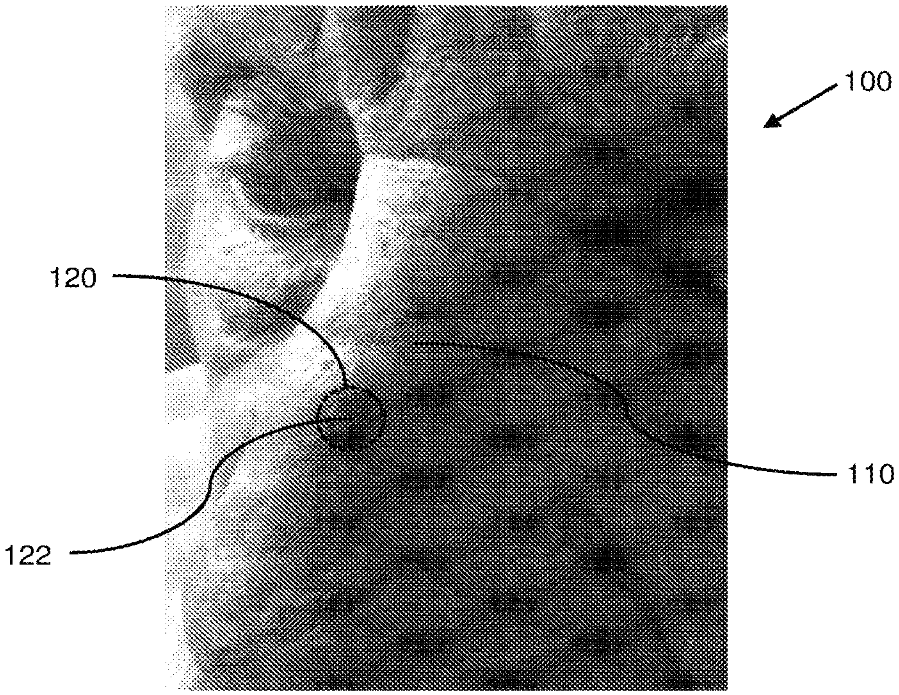
FIG. 1 shows a subject presenting with an open wound.

In the specification and claims, a volume to volume ratio or percentage may be indicated by "(v/v)". A weight to volume ratio or percentage may be indicated by "(w/v)". A weight to weight ratio or percentage may be indicated by "(w/w)". Unless otherwise specified, ratios or percentages are given in relation to the weight or volume of the total composition, as appropriate.

The unit "ppm" refers to "parts per million", and may be used herein to indicate a concentration of a material in a fluid phase. Unless otherwise specified, all values given as ppm are given as weight to volume (w/v) percentages. Accordingly, 1 ppm is equivalent to 1×104% (w/v).

The compositions of the present invention are suitable for topical application. That is, the compositions may be applied to body surfaces such as the skin or mucous membranes.

Base

The composition comprises a base, or carrier. The base is used as a vehicle for the other components of the composition. For the avoidance of doubt, the term 'base' as used herein does not mean a Bronsted-Lowry base or a Lewis base.

The base is preferably a pharmaceutically acceptable base. The nature of the base may influence the formulation of the composition. For example, a suitable base may comprise water (in particular water purified by distillation, ion exchange, reverse osmosis or any other suitable method), or a mixture of water and C1-C4 alkanol. A composition comprising such a base may suitably provide a topically applicable aqueous suspension formulation. Depending on the ratio of water to C1-C4 alkanol, a topically applicable aqueous suspension may be more suitable for spray application (that is, the suspension is applied to the skin as droplets in an aerosol), or may be more suitable for manual application (that is, the user applies the suspension to the skin or mucous membrane with a cloth, pad, or part of their body, for example their hand).

In another example, a suitable base may be an oil, or emulsion of oil and water. In some embodiments, the base may be an ointment base.

Any suitable ointment base may be used. A suitable ointment base may comprise an oleaginous base. Oleaginous bases typically comprise hard paraffin, soft paraffin (also known as petroleum jelly, petrolatum, white petrolatum or multi-hydrocarbon), microcrystalline wax or ceresine. Such bases are typically anhydrous, or have a low water content. These bases may further comprise a film forming agent to provide a protective film after application to the skin. Suitable film forming agents include polyvinylpyrrolidone, polyvinyl alcohol and cellulose derivatives.

Another suitable ointment base may comprise an absorption base (also known as an emulsion base). Absorption ointment bases typically comprise either an oleaginous base as described above and a water-in-oil surfactant, or a hydrophilic oleaginous base, to allow for the formation of a water-in-oil emulsion upon addition of water. Such bases may comprise any of the oleaginous bases described above and/or components selected from: lanolin, beeswax, cetyl alcohol, stearyl alcohol, cetostearyl alcohol, and sodium lauryl ether sulfate. Examples of appropriate absorption bases include hydrophilic petrolatum, anhydrous lanolin, Aquabase®, Aquaphor® and Polysorb®.

Another suitable ointment base may comprise a water-in-oil emulsion base. Water-in-oil emulsion bases typically comprise water and any of the ointment base components described above. In particular, water-in-oil emulsion bases typically comprise a water-in-oil surfactant. Examples of appropriate water-in-oil emulsion bases include cold creams, hydrous lanolin, rose water ointment, aqueous cream, Hydrocream®, Eucerin® and Nivea®.

Another suitable ointment base may comprise an oil-in-water emulsion base. Oil-in-water emulsion bases typically comprise water in an amount greater than that in a water-in-oil emulsion base, and any of the ointment base components described above. In particular, oil-in-water emulsion bases typically comprise an oil-in-water surfactant. Examples of appropriate oil-in-water emulsion bases include hydrophilic ointment, Dermabase®, Velvachol® and Unibase®.

Another suitable ointment base may comprise a water-miscible ointment base. Water-miscible ointment bases typically comprise a combination of low and high molecular weight polyethylene glycols. Examples of appropriate water-miscible ointment bases include PEG ointment and Polybase®.

A composition comprising such ointment bases as described above may suitably provide a topically applicable ointment formulation, or topically applicable cream formulation.

In another example, a suitable base may be a gel. 'Gel' as used herein refers to any dispersion of inorganic or organic molecules in a liquid system wherein there is at least some cross-linking or association between the inorganic or organic molecules. Gels may be prepared by combining a liquid such as water or aqueous Ci-C4 alkanol with suitable gelling agent(s), such as carbomers, carboxymethyl cellulose, ethylcellulose, gelatin, hydroxyethyl cellulose, hydroxypropyl cellulose, magnesium aluminium silicate, methylcellulose, poloxamers, polyvinyl alcohol, sodium alginate, tragacanth, and xanthan gum. A composition comprising such a base may suitably provide a topically applicable gel formulation.

In another example, a suitable base may comprise water and/or Ci-C4 alkanol and a propellant. Suitable propellants may include hydrocarbons, hydrofluorocarbons, and compressed gases. A composition comprising such a base may suitable provide a topically applicable aerosol formulation.

The base may be present in the composition in any suitable amount. Preferably, the base is the majority component of the composition. For example, the base may be present in the composition in an amount of from 80 to 99.9% (v/v), or 85 to 99.5% (v/v), or from 90 to 99% (v/v). The base may be present in the composition in an amount less than or equal to 99.9% (v/v), or 99.5% (v/v), or 99% (v/v), or 98% (v/v), or 97% (v/v), or 96% (v/v), or 95% (v/v), or 90% (v/v). The base may be present in the composition in an amount greater than or equal to 80% (v/v), 85% (v/v), 90%, 95% (v/v), 96% (v/v), 97% (v/v), 98% (v/v), 99% (v/v), 99.5% (v/v), or 99.9% (v/v).

In a preferred embodiment, the base comprises water. In a particular embodiment, the base essentially consists of water.

Silver

The composition also comprises elemental silver as colloidal silver, namely particulate elemental silver dispersed within the base as a colloidal suspension. The silver may be present in the composition in any suitable amount, for example in an amount of from 0.1 ppm to 100 ppm, or from 0.5 ppm to 50 ppm, or from 1 ppm to 10 ppm, or from 5 ppm to 10 ppm; that is, from $1\times10^{-5}$ to $1\times10^{-2}$% (w/v), or from $5\times10^{-5}$ to $5\times10^{-3}$% (w/v), or from $1\times10^{-4}$ to $1\times10^{-3}$% (w/v), or from $5\times10^{-4}$ to $1\times10^{-3}$% (w/v). The silver may be present in the composition in an amount less than or equal to 100 ppm, or 50 ppm, or 10 ppm; that is, less than or equal to $1\times10^{-2}$% (w/v), or $5\times10^{-3}$% (w/v), or $1\times10^{-3}$% (w/v). The silver may be present in the composition in an amount greater than or equal to 0.1 ppm, or 0.5 ppm, or 1 ppm; that is, greater than or equal to $1\times10^{-5}$% (w/v), or $5\times10^{-5}$% (w/v), or $1\times10^{-4}$% (w/v). Suitably, the silver may be present in the composition in an amount of approximately 5 ppm; that is, $5\times10^{-4}$% (w/v).

Plant Extract

Compositions according to the present invention comprise plant extract. A plant extract refers to a substance that has been removed from plant material. Plant extracts may be prepared by treating any plant material with an extractant to extract at least some components of the plant material from the plant material into the extractant. Extractant may be referred to as solvent. The resulting extractant containing at least some components extracted from the plant material is referred to herein as "plant extract". Put another way, "plant extract" may refer to components removed from plant material by treating the plant material with an extractant.

The plant material which is treated with extractant to provide a plant extract may be or derive from any part of a plant, for example, the leaves, bark, roots, seeds or fruits of the plant. In the preparation of plant extract, the plant components extracted from the plant material will be at least partially soluble or suspendable in the extractant. After the plant material has been treated with the extractant, the insoluble plant material may be left in the extractant, or the insoluble plant material may be separated from the extractant. The insoluble plant material may be separated from the extractant according to any appropriate method, for example, decantation, filtration or centrifugation. In preferred embodiments of the present invention, the insoluble plant material has been separated from the extractant; the plant extract does not comprise insoluble components. In a particularly preferred embodiment, the plant extract is prepared by cold percolation extraction. Cold percolation extraction includes placing plant material in a perforated flask or vessel, and treating the plant material with cold extractant. The resulting plant extract will pass through the perforation, leaving the insoluble and/or insuspendable plant material in the flask or vessel.

Suitable plant extract extractants include any which may be used to extract components from the plant material; that is, any extractant in which at least some of the components of the plant material are soluble or suspendable. In one embodiment, the extractant may comprise a C1-C4 alkanol. Suitable C1-C4 alkanols include methanol, ethanol, n-propanol, isopropanol, n-butanol, isobutanol, sec-butanol, and tert-butanol. In one embodiment, the extractant may comprise methanol and/or ethanol. In a particular embodiment, the extractant may comprise ethanol.

In another embodiment, the extractant may comprise acetic acid, glycerine (in particular vegetable glycerine), propylene glycol, honey, or water. Plant extracts may be prepared with hot water or cold water.

The extractant may comprise a combination of extractants. For example, the extractant may comprise a combination of any of the extractants given above. In a particular embodiment, the extractant may comprise water and a C1-C4 alkanol. Such a combination may be referred to as an aqueous C1-C4 alkanol. In a preferred embodiment, the extractant comprises water and ethanol. Such a combination may be referred to as aqueous ethanol.

In a further embodiment, the extractant may essentially consist of any one of the extractants given above, or a combination thereof. In a particular embodiment, the extractant may consist of water and a C1-C4 alkanol. In a preferred embodiment, the extractant consists of water and ethanol.

Aqueous ethanol may have any appropriate ethanol content. For example, the aqueous ethanol may have an ethanol content of from 5 to 95% (v/v), 10 to 90% (v/v), 20 to 80% (v/v), 30 to 70% (v/v), or 40 to 60% (v/v). The aqueous ethanol may have an ethanol content of greater than or equal to 5% (v/v), 10% (v/v), 20% (v/v), 30% (v/v), 40% (v/v), 50% (v/v), 60% (v/v), 70% (v/v), 80% (v/v), 90% (v/v), or 95% (v/v). The aqueous ethanol may have an ethanol content of less than or equal to 95% (v/v), 90% (v/v), 80% (v/v), 70% (v/v), 60% (v/v), 50% (v/v), 40% (v/v), 30% (v/v), 20% (v/v), 10% (v/v), or 5% (v/v).

The plant extracts suitable for use in the present invention may be prepared by treating plant material with extractant in any appropriate ratio. For example, plant extracts for use in the present invention may be prepared by treating plant material with extractant in a ratio of from 2:1 to 1:20 (w/v) plant material to extractant, or from 1:1 to 1:10 (w/v) plant material to extractant, or from 1:2 to 1:9 (w/v) plant material to extractant.

Plant extracts suitable for use in the present invention may be referred to by a variety of names. Plant extracts suitable for use in the present invention particularly include products which may commercially be referred to as extracts (typically an aqueous ethanol extraction of plant material carried out in a ratio of approximately 1:1 (w/v) plant material to extractant), tinctures (typically an aqueous ethanol extraction of plant material carried out in a ratio of approximately 1:3 to 1:5 (w/v) plant material to extractant), mother tinctures (typically an aqueous ethanol extraction of plant material carried out in a ratio of approximately 1:9 (w/v) plant material to extractant), and tisanes such as infusions (typically a hot water extraction of plant material), decoctions (typically an aqueous extraction of plant material carried out in boiling water over an extended period of time) and macerations (typically an extraction of chopped plant material in cold water).

Plant extracts suitable for use with the present invention may be purchased from the vendor G Baldwin & Co.

In some embodiments, the plant extract is an extractant-free extract. That is, a plant extract has been prepared according to the above methods, and then the extractant has been removed to leave a dry substance. The dry substance may correspond to the plant components extracted from the plant material or derivatives thereof only.

The compositions of the present invention comprise plant extract from plants selected from *Equisetum arvense* (also known as common horsetail, or field horsetail), *Rumex crispus* (also known as curly dock, or yellow dock), *Arctium lappa* (also known as burdock, or greater burdock), *Trifolium pratense* (also known as red clover), *Chelidonium majus* (also known as greater celandine, tetterwort, nipplewort, or swallowwort), *Thuja occidentalis* (also known as northern white-cedar or eastern arborvitae), *Urtica dioica* (also known as nettle), *Symphytum officinale* (also known as comfrey, in particular, common comfrey), *Mahonia aquifolium* (also known as Oregon grape), *Echinacea purpurea, Stellaria media* (also known as chickweed), *Galium aparine* (also known as cleavers), *Aloe vera* (also known as *Aloe barbadensis*), *Matricaria recutita* (also known as chamomile), *Hypericum perforatum* (also known as St John's wort), *Calendula officinalis* (also known as common marigold), and *Panax ginseng.*

In some embodiments, the composition may contain other plant extracts in addition to those recited hereinabove. In other embodiments, the composition may contain only the plant extracts recited hereinabove and no other plant extracts.

The composition comprises a combination of extracts from at least 6 plants selected from the group given above. In some embodiments, the composition comprises a combination of extracts from at least 7, 8, 9, 10, 11, 12, 13, 14, 15, 16, or 17 plants selected from the group given above.

Without being bound by theory, it is believed that the combinations of plant extracts with colloidal silver as described herein may provide an alternative or better effect than the corresponding cumulative effect of the plant extracts or colloidal silver used individually.

Given that the plant extract in the composition described herein is invariably an extract from a combination of plants, it may be referred to as 'the plant extract combination'.

Plant extract from a combination of plants can be provided as a single extraction from a combination of plants, or a combination of extracts from individual plants. Preferably, plant extract from a combination of plants is provided as a combination of extracts from individual plants. In embodiments comprising a combination of extracts from individual plants, the extracts from individual plants may be referred to as components of the plant extract combination.

The composition may comprise plant extract in any suitable amount. For example, the composition may comprise plant extract in an amount of from 0.1% to 10% (w/v), or 0.25% to 5% (w/v), or 0.5% to 2.5% (w/v), or 0.75% to 2% (w/v). The plant extract may be present in the composition in an amount less than or equal to 10% (w/v), 5% (w/v), 2.5% (w/v), 2% (w/v), or 1.5% (w/v). The plant extract may be present in the composition in an amount greater than or equal to 0.1% (w/v), or 0.25% (w/v), or 0.5% (w/v), or 0.75% (w/v), or 1% (w/v).

In embodiments wherein the plant extract is provided as a combination of extracts from individual plants, each component of the plant extract may be present in the composition any suitable amount. For example, each component of the plant extract may be present in the composition in an amount of from 0.05% to 10% (w/v), or 0.1% to 5% (w/v), or 0.25% to 2.5% (w/v), or 0.5% to 2% (w/v), or 0.6% (w/v) to 1% (w/v). Each component of the plant extract may be present in the composition in an amount less than or equal to 10% (w/v), 5% (w/v), 2.5% (w/v), 2% (w/v), or 1.5% (w/v), or 1% (w/v). Each component of the plant extract may be present in the composition in an amount greater than or equal to 0.05% (w/v), or 0.1% (w/v), or 0.25% (w/v), or 0.5% (w/v), or 0.6% (w/v), or 0.75% (w/v).

In embodiments wherein the plant extract is provided as an extractant-free plant extract, each component of the extractant-free plant extract may be present in the composition in an amount of from 0.01% to 1% (w/v), or 0.025% to 0.5% (w/v), or 0.05% to 0.25% (w/v), or 0.075% to 0.2% (w/v). The plant extract may be present in the composition in an amount less than or equal to 1% (w/v), 0.5% (w/v), 0.25% (w/v), 0.2% (w/v), or 0.15% (w/v). The plant extract may be present in the composition in an amount greater than or equal to 0.01% (w/v), or 0.025% (w/v), or 0.05% (w/v), or 0.075% (w/v), or 0.1% (w/v).

Plant extracts from individual plants may be combined in any ratio relative to each other to provide the plant extract combination. In some embodiments, the ratio between the component of the plant extract combination present in the largest amount and the component of the plant extract combination present in the smallest amount may be less than 10:1 (w/w), less than 8:1 (w/w), less than 6:1 (w/w), or less than 4:1 (w/w).

Use of Composition

The compositions of the present invention may be suitable for use with humans. For example, the compositions may be suitable for application to the skin and/or mucous membrane of a human body. In other embodiments, the compositions may be suitable for use with non-human animals. For example, the composition may be suitable for application to the skin, mucous membrane, hair and/or coat of animals. The composition may be suitable for application to the skin, mucous membrane, hair and/or coat of non-human animals such as fish, amphibians, reptiles, birds, and non-human mammals. In particular, the composition may be suitable for application to the skin, mucous membrane, hair and/or coat of household pets such as cats, dogs, rabbits, lizards, snakes, parrots, budgerigars and the like. Alternatively or additionally, the composition may be particularly suitable for application to the skin, mucous membrane, hair and/or coat of farmyard animals such as cows, pigs, sheep, horses, goats, donkeys and the like.

The compositions of the present invention may be used as medicaments. The compositions may be used as medicaments for a range of indications, for example dermatitis, psoriasis, wounds, Tinea pedis (also known as Athlete's foot), blisters, insect bites, and inflammation. It may be that one combination of plant extracts is not optimal for treating all of the given indications. Rather, it may be that particular plant extract combinations are particularly suitable for use as medicaments for particular indications.

Particular combinations and the indications they may be particularly suitable for are described herein.

Dermatitis may also be referred to as eczema. Dermatitis includes atopic dermatitis, contact dermatitis, xerotic dermatitis, and seborrhoeic dermatitis. Compositions of the present invention may particularly be used as a medicament for contact dermatitis including irritant diaper dermatitis (also known as nappy rash), and contact dermatitis deriving related to incontinence.

Wounds include open wounds such as incisions, lacerations, abrasions, avulsions, and puncture wounds. Open wounds may also be referred to as severed skin, or cuts. Wounds also include closed wounds such as hematomas. Hematomas include contusions (also referred to as bruises), petechiae, purpura and ecchymoses. Compositions of the present invention may particularly be used as a medicament for open wounds, and/or contusions. Some embodiments may increase the rate of healing of such wounds.

Burns include thermal burns, chemical burns and radiation burns. Compositions of the present invention may particularly be used as a medicament for radiation burns such as sunburn. Alternatively or additionally, compositions of the present invention may particularly be used as a medicament for thermal burns such as oil burns, iron burns, oven burns, and steam burns. Some embodiments may increase the rate of healing of such wounds.

The present invention also relates to a method of treating a dermatological condition. Said method comprises providing a composition as described herein, and applying the composition to the affected area. For example, the method may comprise providing a composition for use as a medicament for dermatitis, and applying said composition to a portion of skin presenting with dermatitis. Alternatively, the method may comprise providing a composition for use as a medicament for psoriasis, and applying said composition to a portion of skin presenting with psoriasis. Alternatively, the method may comprise providing a composition for use as a medicament for wounds, and applying said composition to a wound. Alternatively, the method may comprise providing a composition for use as a medicament for Tinea pedis, and applying said composition to a portion of skin presenting with Tinea pedis. Alternatively, the method may comprise providing a composition for use as a medicament for blisters, and applying said composition to at least part of the surface of the blister. Alternatively, the method may comprise providing a composition for use as a medicament for insect bites, and applying said composition to the insect bite. Alternatively, the method may comprise providing a composition for use as a medicament for inflammation, and applying said composition to a portion of inflamed skin.

The composition of the present invention may alternatively or additionally be a cosmetic composition. For instance, compositions may be applied to the skin to reduce the size and/or pigmentation of nevi (also known as moles), liver spots, areas of hyperpigmentation, reddened skin, and rashes.

The present invention also relates to non-therapeutic cosmetic methods. Said method comprises providing a composition as described herein, selecting an area of the body to which the composition should be applied, and topically applying the composition to the selected area. For example, the method may comprise providing a composition, selecting a nevi, and applying said composition to at least part of the surface of the nevi. Alternatively, the method may comprise providing a composition, selecting a liver spot, and applying said composition to at least part of the surface of the liver spot. Alternatively, the method may comprise providing a composition, selecting an area of hyperpigmentation, and applying said composition to at least part of the surface of the area of hyperpigmentation. Alternatively, the method may comprise providing a composition, selecting an area of reddened skin, and applying said composition to at least part of the surface of the reddened skin. Alternatively, the method may comprise providing a composition, selecting a rash, and applying said composition to at least part of the surface of the rash.

Compositions may also be used for providing the user with a sensation at the skin and/or mucous membrane. For example, application of the composition to the skin and/or mucous membrane may result in the user perceiving a cooling and/or soothing sensation.

The composition of the present invention may alternatively or additionally be used on the skin and/or hair of household pets such as cats, dogs etc.

The compositions of the present invention may be provided to the user in any form. For example, the composition may be provided alone, or in combination with a form of application. For example, in one embodiment, there is provided a dressing comprising a composition as described herein. In another embodiment, there is provided a porous sheet impregnated with a composition as described herein. Such an impregnated porous sheet may be referred to as a "wet wipe".

Specific Combinations of Components

In a particular embodiment, the composition comprises water in an amount of from 80 to 99.9% (v/v). The composition also comprises elemental silver as a colloidal suspension in an amount 15 of from 0.1 ppm to 100 ppm (that is, $1\times10^{-5}$ to $1\times10^{-2}$% (w/v). The composition also comprises plant extract from at least 6 plants selected from the group consisting of *Equisetum arvense, Rumex crispus, Arctium lappa, Trifolium pratense, Chelidonium majus, Thuja occidentalis, Urtica dioica, Symphytum officinale, Mahonia aquifolium, Echinacea purpurea, Stellaria media, Galium aparine, Aloe vera, Matricaria recutita, Hypericum perforatum, Calendula officinalis*, and *Panax ginseng*. The plant extract is present in the composition in an amount of from 0.1% to 10% (w/v).

In a further embodiment, the composition consists of elemental silver in an amount of from $1\times10^{-5}$% to $1\times10^{-2}$% (w/v), plant extract in an amount of from 0.1% to 10% (w/v), and water as the remainder of the composition up to 100%.

In one embodiment, the plant extract may comprise or consist of extracts from *Equisetum arvense, Symphytum officinale, Mahonia aquifolium, Matricaria recutita, Hypericum perforatum, Calendula officinalis*, and *Panax ginseng*. This embodiment may be particularly suitable for use as a medicament for blisters.

In a further embodiment, the composition may consist of elemental silver in an amount of from $1\times10^{-5}$% to $1\times10^{-2}$% (w/v), plant extract comprising or consisting of extracts from *Equisetum arvense, Symphytum officinale, Mahonia aquifolium, Matricaria recutita, Hypericum perforatum, Calendula officinalis*, and *Panax ginseng* in an amount of from 0.1% to 10% (w/v), and water as the remainder of the composition up to 100%.

In one embodiment, the plant extract may comprise or consist of extracts from *Arctium lappa, Echinacea purpurea, Stellaria media, Matricaria recutita, Hypericum perforatum*, and *Calendula officinalis*. This embodiment may be particularly suitable for use as a cosmetic composition to be applied to skin blemishes.

In a further embodiment, the composition may consist of elemental silver in an amount of from $1\times10^{-5}$% to $1\times10^{-2}$% (w/v), plant extract comprising or consisting of extracts from *Arctium lappa, Echinacea purpurea, Stellaria media, Matricaria recutita, Hypericum perforatum*, and *Calendula officinalis* in an amount of from 0.1% to 10% (w/v), and water as the remainder of the composition up to 100%.

In one embodiment, the plant extract may comprise or consist of extracts from *Symphytum officinale, Echinacea purpurea, Aloe vera, Matricaria recutita, Hypericum perforatum, Calendula officinalis*, and *Panax ginseng*. This embodiment may be particularly suitable for use as a medicament for burns.

In a further embodiment, the composition may consist of elemental silver in an amount of from $1\times10^{-5}$% to $1\times10^{-2}$% (w/v), plant extract comprising or consisting of extracts from *Symphytum officinale, Echinacea purpurea, Aloe vera, Matricaria recutita, Hypericum perforatum, Calendula officinalis*, and *Panax ginseng* in an amount of from 0.1% to 10% (w/v), and water as the remainder of the composition up to 100%.

In one embodiment, the plant extract may comprise or consist of extracts from *Galium aparine, Aloe vera, Matricaria recutita, Hypericum perforatum, Calendula officinalis*, and *Panax ginseng*. This embodiment may be particularly suitable for use as a medicament for sunburn.

In a further embodiment, the composition may consist of elemental silver in an amount of from $1\times10^{-5}$% to $1\times10^{-2}$% (w/v), plant extract comprising or consisting of extracts from *Galium aparine, Aloe vera, Matricaria recutita, Hypericum perforatum, Calendula officinalis*, and *Panax ginseng* in an amount of from 0.1% to 10% (w/v), and water as the remainder of the composition up to 100%.

In one embodiment, the plant extract may comprise extracts from *Equisetum arvense, Rumex crispus, Arctium lappa, Trifolium pratense, Chelidonium majus, Thuja occidentalis, Urtica dioica, Symphytum officinale, Mahonia aquifolium, Echinacea purpurea, Stellaria media, Galium aparine, Aloe vera, Matricaria recutita, Hypericum perforatum, Calendula officinalis*, and *Panax ginseng*. This embodiment may be particularly suitable for use as a medicament for eczema.

In a further embodiment, the composition may consist of elemental silver in an amount of from $1\times10^{-5}$% to $1\times10^{-2}$% (w/v), plant extract comprising or consisting of extracts from *Equisetum arvense, Rumex crispus, Arctium lappa, Trifolium pratense, Chelidonium majus, Thuja occidentalis,*

*Urtica dioica, Symphytum officinale, Mahonia aquifolium, Echinacea purpurea, Stellaria media, Galium aparine, Aloe vera, Matricaria recutita, Hypericum perforatum, Calendula officinalis,* and *Panax ginseng* in an amount of from 0.1% to 10% (w/v), and water as the remainder of the composition up to 100%.

In one embodiment, the plant extract may comprise or consist of extracts from *Equisetum arvense, Symphytum officinale, Echinacea purpurea, Stellaria media, Aloe vera, Matricaria recutita, Hypericum perforatum, Calendula officinalis,* and *Panax ginseng*. This embodiment may be particularly suitable for use as a medicament for open wounds.

In a further embodiment, the composition may consist of elemental silver in an amount of from $1\times10^{-5}$% to $1\times10^{-2}$% (w/v), plant extract comprising or consisting of extracts from *Equisetum arvense, Symphytum officinale, Echinacea purpurea, Stellaria media, Aloe vera, Matricaria recutita, Hypericum perforatum, Calendula officinalis,* and *Panax ginseng* in an amount of from 0.1% to 10% (w/v), and water as the remainder of the composition up to 100%.

In one embodiment, the plant extract may comprise or consist of extracts from *Chelidonium majus, Thuja occidentalis, Echinacea purpurea, Galium aparine, Matricaria recutita, Hypericum perforatum,* and *Calendula officinalis*. This embodiment may be particularly suitable for use as a medicament for *Tinea pedis*.

In a further embodiment, the composition may consist of elemental silver in an amount of from $1\times10^{-5}$% to $1\times10^{-2}$% (w/v), plant extract comprising or consisting of extracts from *Chelidonium majus, Thuja occidentalis, Echinacea purpurea, Galium aparine, Matricaria recutita, Hypericum perforatum,* and *Calendula officinalis* in an amount of from 0.1% to 10% (w/v), and water as the remainder of the composition up to 100%.

In one embodiment, the plant extract may comprise or consist of extracts from *Chelidonium majus, Thuja occidentalis, Mahonia aquifolium, Aloe vera, Matricaria recutita,* and *Calendula officinalis*. This embodiment may be particularly suitable for use as a cosmetic composition to be applied to nevi.

In a further embodiment, the composition may consist of elemental silver in an amount of from $1\times10^{-5}$% to $1\times10^{-2}$% (w/v), plant extract comprising or consisting of extracts from *Chelidonium majus, Thuja occidentalis, Mahonia aquifolium, Aloe vera, Matricaria recutita,* and *Calendula officinalis* in an amount of from 0.1% to 10% (w/v), and water as the remainder of the composition up to 100%.

In one embodiment, the plant extract may comprise or consist of extracts from *Arctium lappa, Urtica dioica, Echinacea purpurea, Stellaria media, Matricaria recutita, Hypericum perforatum,* and *Calendula officinalis*. This embodiment may be particularly suitable for use as a medicament for insect bites.

In a further embodiment, the composition may consist of elemental silver in an amount of from $1\times10^{-5}$% to $1\times10^{-2}$% (w/v), plant extract comprising or consisting of extracts from *Arctium lappa, Urtica dioica, Echinacea purpurea, Stellaria media, Matricaria recutita, Hypericum perforatum,* and *Calendula officinalis* in an amount of from 0.1% to 10% (w/v), and water as the remainder of the composition up to 100%.

In one embodiment, the plant extract may comprise or consist of extracts from *Urtica dioica, Symphytum officinale, Echinacea purpurea, Stellaria media, Aloe vera, Matricaria recutita,* and *Calendula officinalis*. This embodiment may be particularly suitable for use as a medicament for irritant diaper dermatitis.

In a further embodiment, the composition may consist of elemental silver in an amount of from $1\times10^{-5}$% to $1\times10^{-2}$% (w/v), plant extract comprising or consisting of extracts from *Urtica dioica, Symphytum officinale, Echinacea purpurea, Stellaria media, Aloe vera, Matricaria recutita,* and *Calendula officinalis* in an amount of from 0.1% to 10% (w/v), and water as the remainder of the composition up to 100%.

In one embodiment, the plant extract may comprise or consist of extracts from *Urtica dioica, Symphytum officinale, Mahonia aquifolium, Echinacea purpurea, Stellaria media, Aloe vera, Matricaria recutita, Hypericum perforatum, Calendula officinalis,* and *Panax ginseng*. This embodiment may be particularly suitable for use as a medicament for contact dermatitis deriving from incontinence.

In a further embodiment, the composition may consist of elemental silver in an amount of from $1\times10^{-5}$% to $1\times10^{-2}$% (w/v), plant extract comprising or consisting of extracts from *Urtica dioica, Symphytum officinale, Mahonia aquifolium, Echinacea purpurea, Stellaria media, Aloe vera, Matricaria recutita, Hypericum perforatum, Calendula officinalis,* and *Panax ginseng* in an amount of from 0.1% to 10% (w/v), and water as the remainder of the composition up to 100%.

In one embodiment, the plant extract may comprise or consist of extracts from *Rumex crispus, Arctium lappa, Trifolium pratense, Symphytum officinale, Echinacea purpurea, Stellaria media, Hypericum perforatum, Calendula officinalis,* and *Panax ginseng*. This embodiment may be particularly suitable for application to the skin and hair of household pets.

In a further embodiment, the composition may consist of elemental silver in an amount of from $1\times10^{-5}$% to $1\times10^{-2}$% (w/v), plant extract comprising or consisting of extracts from *Rumex crispus, Arctium lappa, Trifolium pratense, Symphytum officinale, Echinacea purpurea, Stellaria media, Hypericum perforatum, Calendula officinalis,* and *Panax ginseng* in an amount of from 0.1% to 10% (w/v), and water as the remainder of the composition up to 100%.

In one embodiment, the plant extract may comprise or consist of extracts from *Urtica dioica, Symphytum officinale, Echinacea purpurea, Stellaria media, Aloe vera, Matricaria recutita,* and *Calendula officinalis*. This embodiment may be particularly suitable for including in a porous sheet (also known as a wet wipe).

In a further embodiment, the composition may consist of elemental silver in an amount of from $1\times10^{-5}$% to $1\times10^{-2}$% (w/v), plant extract comprising or consisting of extracts from *Urtica dioica, Symphytum officinale, Echinacea purpurea, Stellaria media, Aloe vera, Matricaria recutita,* and *Calendula officinalis* in an amount of from 0.1% to 10% (w/v), and water as the remainder of the composition up to 100%.

In one embodiment, the plant extract may comprise or consist of extracts from *Rumex crispus, Arctium lappa, Trifolium pratense, Symphytum officinale, Echinacea purpurea, Stellaria media, Matricaria recutita,* and *Calendula officinalis*. This embodiment may be particularly suitable for including in a porous sheet (also known as a wet wipe), for application to the skin and hair of household pets.

In a further embodiment, the composition may consist of elemental silver in an amount of from $1\times10^{-5}$% to $1\times10^{-2}$% (w/v), plant extract comprising or consisting of extracts from *Rumex crispus, Arctium lappa, Trifolium pratense, Symphytum officinale, Echinacea purpurea, Stellaria media,*

*Matricaria recutita,* and *Calendula officinalis* in an amount of from 0.1% to 10% (w/v), and water as the remainder of the composition up to 100%.

Methods of Preparing Compositions

Compositions according to the present invention may be manufactured according to any suitable method. One appropriate method is to provide plant extract from at least 6 plants selected from the group consisting of *Equisetum arvense, Rumex crispus, Arctium lappa, Trifolium pratense, Chelidonium majus, Thuja occidentalis, Urtica dioica, Symphytum officinale, Mahonia aquifolium, Echinacea purpurea, Stellaria media, Galium aparine, Aloe vera, Matricaria recutita, Hypericum perforatum, Calendula officinalis,* and *Panax ginseng*. The method further comprises providing a colloidal suspension of silver in a base, the silver content of the colloidal suspension being of from 0.1 ppm to 100 ppm (that is, $1\times10^{-5}$% to $1\times10^{-2}$% (w/v) of the base). The plant extract and colloidal suspension are then combined to provide a composition for topical application.

The base may be any of those described herein. In one embodiment, the base is water.

The plant extract and colloidal suspension of silver may be combined in any appropriate ratio. In one embodiment, they are combined in a ratio of from 1:20 to 1:4 (w/v) plant extract to colloidal suspension of silver, or from 1:15 to 1:6, or from 1:12 to 1:8. In one embodiment, they are combined in a ratio of around 1:9 (w/v) plant extract to colloidal suspension of silver.

EXAMPLES

Examples 1 to 14 provide topically applicable compositions comprising plant extracts prepared by extracting plant material with aqueous ethanol in a ratio of 1:1 weight/volume plant material to aqueous ethanol. The proportion of ethanol to water in the aqueous ethanol (i.e. the ethanol content) for each extract is as follows:

TABLE 1

| Plant material | % ethanol to water (v/v) |
|---|---|
| *Equisetum arvense* | 25% |
| *Rumex crispus* | 45% |
| *Arctium lappa* | 45% |
| *Trifolium pratense* | 45% |
| *Chelidonium majus* | 45% |
| *Thuja occidentalis* | 45% |
| *Urtica dioica* | 45% |
| *Symphytum officinale* | 45% |
| *Mahonia aquifolium* | 45% |
| *Echinacea purpurea* | 45% |
| *Stellaria media* | 45% |
| *Galium aparine* | 45% |
| *Aloe vera* | 60% |
| *Matricaria recutita* | 45% |
| *Hypericum perforatum* | 60% |
| *Calendula officinalis* | 90% |
| *Panax ginseng* | 45% |

Example 1

This is an example of a composition for applying to blisters.

Aqueous extracts of *Equisetum arvense* (0.20 mL), *Symphytum officinale* (0.40 mL), *Mahonia aquifolium* (0.20 mL), *Matricaria recutita* (0.20 mL), *Hypericum perforatum* (0.12 mL), *Calendula officinalis* (0.20 mL), and *Panax ginseng* (0.20 mL) were combined in a vessel. The extract combination was then made up to 100 mL by the addition of 5 ppm aqueous colloidal silver to provide a topically applicable composition.

Example 2

This is an example of a composition for applying to skin blemishes.

Aqueous extracts of *Arctium lappa* (0.20 mL), *Echinacea purpurea* (0.40 mL), *Stellaria media* (0.20 mL), *Matricaria recutita* (0.20 mL), *Hypericum perforatum* (0.12 mL), and *Calendula officinalis* (0.12 mL) were combined in a vessel. The extract combination was then made up to 100 mL by the addition of 5 ppm aqueous colloidal silver to provide a topically applicable composition.

Example 3

This is an example of a composition for applying to skin burns.

Aqueous extracts of *Symphytum officinale* (0.28 mL), *Echinacea purpurea* (0.12 mL), *Aloe vera* (0.20 mL), *Matricaria recutita* (0.20 mL), *Hypericum perforatum* (0.20 mL), *Calendula officinalis* (0.20 mL), and *Panax ginseng* (0.28 mL) were combined in a vessel. The extract combination was then made up to 100 mL by the addition of 5 ppm aqueous colloidal silver to provide a topically applicable composition.

Example 4

This is an example of a composition for applying to eczema.

Aqueous extracts of *Equisetum arvense* (0.20 mL), *Rumex crispus* (0.20 mL), *Arctium lappa* (0.08 mL), *Trifolium pratense* (0.28 mL), *Chelidonium majus* (0.08 mL), *Thuja occidentalis* (0.08 mL), *Urtica dioica* (0.12 mL), *Symphytum officinale* (0.20 mL), *Mahonia aquifolium* (0.20 mL), *Echinacea purpurea* (0.20 mL), *Stellaria media* (0.28 mL), *Galium aparine* (0.28 mL), *Aloe vera* (0.20 mL), *Matricaria recutita* (0.20 mL), *Hypericum perforatum* (0.12 mL), *Calendula officinalis* (0.12 mL), and *Panax ginseng* (0.20 mL) were combined in a vessel. The extract combination was then made up to 100 mL by the addition of 5 ppm aqueous colloidal silver to provide a topically applicable composition.

Example 5

This is an example of a composition for applying to cuts.

Aqueous extracts of *Equisetum arvense* (0.20 mL), *Symphytum officinale* (0.28 mL), *Echinacea purpurea* (0.20 mL), *Stellaria media* (0.12 mL), *Aloe vera* (0.20 mL), *Matricaria recutita* (0.12 mL), *Hypericum perforatum* (0.12 mL), *Calendula officinalis* (0.28 mL), and *Panax ginseng* (0.28 mL) were combined in a vessel. The extract combination was then made up to 100 mL by the addition of 5 ppm aqueous colloidal silver to provide a topically applicable composition.

Example 6

This is an example of a composition for applying to Tinea pedis (Athlete's Foot). Aqueous extracts of *Chelidonium majus* (0.04 mL), *Thuja occidentalis* (0.20 mL), *Echinacea purpurea* (0.12 mL), *Galium aparine* (0.40 mL), *Matricaria recutita* (0.40 mL), *Hypericum perforatum* (0.12 mL), and

*Calendula officinalis* (0.28 mL) were combined in a vessel. The extract combination was then made up to 100 mL by the addition of 5 ppm aqueous colloidal silver to provide a topically applicable composition.

Example 7

This is an example of a composition for applying to sunburn.

Aqueous extracts of *Galium aparine* (0.20 mL) *Aloe vera* (0.28 mL), *Matricaria recutita* (0.20 mL), *Hypericum perforatum* (0.28 mL), *Calendula officinalis* (0.28 mL), and *Panax ginseng* (0.20 mL) were combined in a vessel. The extract combination was then made up to 100 mL by the addition of 5 ppm aqueous colloidal silver to provide a topically applicable composition.

Example 8

This is an example of a composition for applying to moles.

Aqueous extracts of *Chelidonium majus* (0.12 mL), *Thuja occidentalis* (0.28 mL), *Mahonia aquifolium* (0.20 mL), *Aloe vera* (0.30 mL), *Matricaria recutita* (0.20 mL), and *Calendula officinalis* (0.28 mL) were combined in a vessel. The extract combination was then made up to 100 mL by the addition of 5 ppm aqueous colloidal silver to provide a topically applicable composition.

Example 9

This is an example of a composition for applying to insect bites.

Aqueous extracts of *Arctium lappa* (0.20 mL), *Urtica dioica* (0.28 mL), *Echinacea purpurea* (0.28 mL), *Stellaria media* (0.20 mL), *Matricaria recutita* (0.12 mL), *Hypericum perforatum* (0.20 mL), and *Calendula officinalis* (0.28 mL) were combined in a vessel. The extract combination was then made up to 100 mL by the addition of 5 ppm aqueous colloidal silver to provide a topically applicable composition.

Example 10

This is an example of a composition for applying to irritant diaper dermatitis.

Aqueous extracts of *Urtica dioica* (0.20 mL), *Symphytum officinale* (0.28 mL), *Echinacea purpurea* (0.28 mL), *Stellaria media* (0.20 mL), *Aloe vera* (0.28 mL), *Matricaria recutita* (0.28 mL), and *Calendula officinalis* (0.28 mL) were combined in a vessel. The extract combination was then made up to 100 mL by the addition of 5 ppm aqueous colloidal silver to provide a topically applicable composition.

Example 11

This is an example of a composition for use in the treatment of contact dermatitis related to incontinence.

Aqueous extracts of *Urtica dioica* (0.20 mL), *Symphytum officinale* (0.28 mL), *Echinacea purpurea* (0.20 mL), *Mahonia aquifolium* (0.12 mL), *Stellaria media* (0.20 mL), *Aloe vera* (0.28 mL), *Matricaria recutita* (0.28 mL), *Hypericum perforatum* (0.20 mL), *Calendula officinalis* (0.28 mL), and *Panax ginseng* (0.28 mL) were combined in a vessel. The extract combination was then made up to 100 mL by the addition of 5 ppm aqueous colloidal silver to provide a topically applicable composition.

Example 12

This is an example of a composition for applying to the skin of household pets.

Aqueous extracts of *Rumex crispus* (0.20 mL), *Arctium lappa* (0.20 mL), *Trifolium pratense* (0.20 mL), *Symphytum officinale* (0.12 mL), *Echinacea purpurea* (0.20 mL), *Stellaria media* (0.12 mL), *Hypericum perforatum* (0.12 mL), *Calendula officinalis* (0.12 mL), and *Panax ginseng* (0.12 mL) were combined in a vessel. The extract combination was then made up to 100 mL by the addition of 5 ppm aqueous colloidal silver to provide a topically applicable composition.

Example 13

This is an example of a composition suitable to be provided in combination with a form of application, such as a porous sheet impregnated with the composition.

Aqueous extracts of *Urtica dioica* (0.20 mL), *Symphytum officinale* (0.28 mL), *Echinacea purpurea* (0.20 mL), *Stellaria media* (0.20 mL), *Aloe vera* (0.28 mL), *Matricaria recutita* (0.28 mL), and *Calendula officinalis* (0.28 mL), were combined in a vessel. The extract combination was then made up to 100 mL by the addition of 5 ppm aqueous colloidal silver to provide a composition. A porous sheet was treated with the resulting composition to provide a porous sheet impregnated with the composition (a "wet wipe").

Example 14

This is an example of a composition suitable to be provided in combination with a form of application, such as a porous sheet impregnated with the composition, wherein the composition is suitable for use with household pets.

Aqueous extracts of *Rumex crispus* (0.20 mL), *Arctium lappa* (0.20 mL), *Trifolium pratense* (0.20 mL), *Symphytum officinale* (0.12 mL), *Echinacea purpurea* (0.20 mL), *Stellaria media* (0.12 mL), *Matricaria recutita* (0.12 mL), and *Calendula officinalis* (0.12 mL) were combined in a vessel.

The extract combination was then made up to 100 mL by the addition of 5 ppm aqueous colloidal silver to provide a composition. A porous sheet was treated with the resulting composition to provide a porous sheet impregnated with the composition (a "wet wipe").

Examples 15 to 28 provide topically applicable compositions comprising mother tinctures prepared by extracting plant material with aqueous ethanol in a ratio of 1:9 weight/volume plant material to aqueous ethanol. The proportion of ethanol to water in the aqueous ethanol (i.e. the ethanol content) for each extract is as follows:

TABLE 2

| Plant material | % ethanol to water (v/v) |
|---|---|
| *Equisetum arvense* | 52% |
| *Rumex crispus* | 49% |
| *Arctium lappa* | 53% |
| *Trifolium pratense* | 63% |
| *Chelidonium majus* | 62% |
| *Thuja occidentalis* | 64% |
| *Urtica dioica* | 49% |
| *Symphytum officinale* | 41% |
| *Mahonia aquifolium* | 69% |

TABLE 2-continued

| Plant material | % ethanol to water (v/v) |
|---|---|
| *Echinacea purpurea* | 64% |
| *Stellaria media* | 50% |
| *Galium aparine* | 49% |
| *Aloe vera* | 0% |
| *Matricaria recutita* | 65% |
| *Hypericum perforatum* | 65% |
| *Calendula officinalis* | 64% |
| *Panax ginseng* | 89% |

Example 15

This is an example of a composition for applying to blisters.

Aqueous ethanol extracts of *Equisetum arvense* (0.32 mL), *Symphytum officinale* (0.40 mL), *Mahonia aquifolium* (0.32 mL), *Matricaria recutita* (0.32 mL), *Hypericum perforatum* (0.20 mL), *Calendula officinalis* (0.32 mL), and *Panax ginseng* (0.20 mL) were combined in a vessel. The extract combination was then made up to 100 mL by the addition of 5 ppm aqueous colloidal silver to provide a topically applicable composition.

Example 16

This is an example of a composition for applying to skin blemishes.

Aqueous ethanol extracts of *Arctium lappa* (0.32 mL), *Echinacea purpurea* (0.40 mL), *Stellaria media* (0.32 mL), *Matricaria recutita* (0.32 mL), *Hypericum perforatum* (0.20 mL), and *Calendula officinalis* (0.20 mL) were combined in a vessel. The extract combination was then made up to 100 mL by the addition of 5 ppm aqueous colloidal silver to provide a topically applicable composition.

Example 17

This is an example of a composition for applying to skin burns.

Aqueous ethanol extracts of *Symphytum officinale* (0.40 mL), *Echinacea purpurea* (0.20 mL), *Aloe vera* (0.32 mL), *Matricaria recutita* (0.32 mL), *Hypericum perforatum* (0.32 mL), *Calendula officinalis* (0.32 mL), and *Panax ginseng* (0.40 mL) were combined in a vessel. The extract combination was then made up to 100 mL by the addition of 5 ppm aqueous colloidal silver to provide a topically applicable composition.

Example 18

This is an example of a composition for applying to eczema.

Aqueous ethanol extracts of *Equisetum arvense* (0.32 mL), *Rumex crispus* (0.32 mL), *Arctium lappa* (0.08 mL), *Trifolium pratense* (0.40 mL), *Chelidonium majus* (0.08 mL), *Thuja occidentalis* (0.08 mL), *Urtica dioica* (0.20 mL), *Symphytum officinale* (0.32 mL), *Mahonia aquifolium* (0.32 mL), *Echinacea purpurea* (0.20 mL), *Stellaria media* (0.40 mL), *Galium aparine* (0.40 mL), *Aloe vera* (0.32 mL), *Matricaria recutita* (0.32 mL), *Hypericum perforatum* (0.20 mL), *Calendula officinalis* (0.20 mL), and *Panax ginseng* (0.32 mL) were combined in a vessel. The extract combination was then made up to 100 mL by the addition of 5 ppm aqueous colloidal silver to provide a topically applicable composition.

Example 19

This is an example of a composition for applying to cuts.

Aqueous ethanol extracts of *Equisetum arvense* (0.32 mL), *Symphytum officinale* (0.40 mL), *Echinacea purpurea* (0.32 mL), *Stellaria media* (0.20 mL), *Aloe vera* (0.32 mL), *Matricaria recutita* (0.20 mL), *Hypericum perforatum* (0.20 mL), *Calendula officinalis* (0.40 mL), and *Panax ginseng* (0.40 mL) were combined in a vessel. The extract combination was then made up to 100 mL by the addition of 5 ppm aqueous colloidal silver to provide a topically applicable composition.

Example 20

This is an example of a composition for applying to Tinea pedis (Athlete's Foot).

Aqueous ethanol extracts of *Chelidonium majus* (0.12 mL), *Thuja occidentalis* (0.32 mL), *Echinacea purpurea* (0.20 mL), *Galium aparine* (0.40 mL), *Matricaria recutita* (0.40 mL), *Hypericum perforatum* (0.20 mL), and *Calendula officinalis* (0.40 mL), were combined in a vessel. The extract combination was then made up to 100 mL by the addition of 5 ppm aqueous colloidal silver to provide a topically applicable composition.

Example 21

This is an example of a composition for applying to sunburn.

Aqueous ethanol extracts of *Galium aparine* (0.32 mL), *Aloe vera* (0.40 mL), *Matricaria recutita* (0.32 mL), *Hypericum perforatum* (0.40 mL), *Calendula officinalis* (0.40 mL), and *Panax ginseng* (0.32 mL), were combined in a vessel. The extract combination was then made up to 100 mL by the addition of 5 ppm aqueous colloidal silver to provide a topically applicable composition.

Example 22

This is an example of a composition for applying to moles.

Aqueous ethanol extracts of *Chelidonium majus* (0.20 mL), *Thuja occidentalis* (0.40 mL), *Mahonia aquifolium* (0.20 mL), *Aloe vera* (0.20 mL), *Matricaria recutita* (0.20 mL), and *Calendula officinalis* (0.40 mL) were combined in a vessel. The extract combination was then made up to 100 mL by the addition of 5 ppm aqueous colloidal silver to provide a topically applicable composition.

Example 23

This is an example of a composition for applying to insect bites.

Aqueous ethanol extracts of *Arctium lappa* (0.32 mL), *Urtica dioica* (0.40 mL), *Echinacea purpurea* (0.40 mL), *Stellaria media* (0.32 mL), *Matricaria recutita* (0.20 mL), *Hypericum perforatum* (0.32 mL), and *Calendula officinalis* (0.40 mL) were combined in a vessel. The extract combination was then made up to 100 mL by the addition of 5 ppm aqueous colloidal silver to provide a topically applicable composition.

Example 24

This is an example of a composition for applying to irritant diaper dermatitis.

Aqueous ethanol extracts of *Urtica dioica* (0.32 mL), *Symphytum officinale* (0.40 mL), *Echinacea purpurea* (0.32 mL), *Stellaria media* (0.32 mL), *Aloe vera* (0.40 mL), *Matricaria recutita* (0.40 mL), and *Calendula officinalis* (0.40 mL) were combined in a vessel. The extract combination was then made up to 100 mL by the addition of 5 ppm aqueous colloidal silver to provide a topically applicable composition.

Example 25

This is an example of a composition for use in the treatment of contact dermatitis related to incontinence.

Aqueous ethanol extracts of *Urtica dioica* (0.32 mL), *Symphytum officinale* (0.40 mL), *Mahonia aquifolium* (0.20 mL), *Echinacea purpurea* (0.40 mL), *Stellaria media* (0.32 mL), *Aloe vera* (0.32 mL), *Matricaria recutita* (0.40 mL), *Hypericum perforatum* (0.32 mL), *Calendula officinalis* (0.32 mL), and *Panax ginseng* (0.40 mL) were combined in a vessel. The extract combination was then made up to 100 mL by the addition of 5 ppm aqueous colloidal silver to provide a topically applicable composition.

Example 26

This is an example of a composition for applying to the skin of household pets.

Aqueous ethanol extracts of *Rumex crispus* (0.32 mL), *Arctium lappa* (0.32 mL), *Trifolium pratense* (0.32 mL), *Symphytum officinale* (0.20 mL), *Echinacea purpurea* (0.32 mL), *Stellaria media* (0.20 mL), *Hypericum perforatum* (0.20 mL), *Calendula officinalis* (0.20 mL), and *Panax ginseng* (0.20 mL) were combined in a vessel. The extract combination was then made up to 100 mL by the addition of 5 ppm aqueous colloidal silver to provide a topically applicable composition.

Example 27

This is an example of a composition suitable to be provided in combination with a form of application, such as a porous sheet impregnated with the composition.

Aqueous ethanol extracts of *Urtica dioica* (0.20 mL), *Symphytum officinale* (0.40 mL), *Echinacea purpurea* (0.32 mL), *Stellaria media* (0.32 mL), *Aloe vera* (0.40 mL), *Matricaria recutita* (0.40 mL), and *Calendula officinalis* (0.40 mL), were combined in a vessel. The extract combination was then made up to 100 mL by the addition of 5 ppm aqueous colloidal silver to provide a composition. A porous sheet was treated with the resulting composition to provide a porous sheet impregnated with the composition (a "wet wipe").

Example 28

This is an example of a composition suitable to be provided in combination with a form of application, such as a porous sheet impregnated with the composition, wherein the composition is suitable for use with household pets.

*Rumex crispus* (0.32 mL), *Arctium lappa* (0.32 mL), *Trifolium pratense* (0.32 mL), *Symphytum officinale* (0.20 mL), *Echinacea purpurea* (0.32 mL), *Stellaria media* (0.20 mL), *Matricaria recutita* (0.20 mL), and *Calendula officinalis* (0.20 mL) were combined in a vessel. The extract combination was then made up to 100 mL by the addition of 5 ppm aqueous colloidal silver to provide a composition. A porous sheet was treated with the resulting composition to provide a porous sheet impregnated with the composition (a "wet wipe").

Examples 29 to 42 provide topically applicable compositions comprising plant tinctures prepared by extracting plant material with aqueous ethanol in a ratio of 1:3 weight/volume plant material to aqueous ethanol. The proportion of ethanol to water in the aqueous ethanol (i.e. the ethanol content) for each extract is that as given in Table 1 hereinabove.

Example 29

This is an example of a composition for applying to blisters.

Aqueous extracts of *Equisetum arvense* (0.60 mL), *Symphytum officinale* (0.40 mL), *Mahonia aquifolium* (0.60 mL), *Matricaria recutita* (0.60 mL), *Hypericum perforatum* (0.40 mL), *Calendula officinalis* (0.60 mL), and *Panax ginseng* (0.20 mL) were combined in a vessel. The extract combination was then made up to 100 mL by the addition of 5 ppm aqueous colloidal silver to provide a topically applicable composition.

Example 30

This is an example of a composition for applying to skin blemishes.

Aqueous extracts of *Arctium lappa* (0.60 mL), *Echinacea purpurea* (0.40 mL), *Stellaria media* (0.60 mL), *Matricaria recutita* (0.60 mL), *Hypericum perforatum* (0.40 mL), and *Calendula officinalis* (0.40 mL) were combined in a vessel. The extract combination was then made up to 100 mL by the addition of 5 ppm aqueous colloidal silver to provide a topically applicable composition.

Example 31

This is an example of a composition for applying to skin burns.

Aqueous extracts of *Symphytum officinale* (0.80 mL), *Echinacea purpurea* (0.40 mL), *Aloe vera* (0.60 mL), *Matricaria recutita* (0.60 mL), *Hypericum perforatum* (0.60 mL), *Calendula officinalis* (0.60 mL), and *Panax ginseng* (0.80 mL) were combined in a vessel. The extract combination was then made up to 100 mL by the addition of 5 ppm aqueous colloidal silver to provide a topically applicable composition.

Example 32

This is an example of a composition for applying to eczema.

Aqueous extracts of *Equisetum arvense* (0.60 mL), *Rumex crispus* (0.60 mL), *Arctium lappa* (0.04 mL), *Trifolium pratense* (0.80 mL), *Chelidonium majus* (0.04 mL), *Thuja occidentalis* (0.04 mL), *Urtica dioica* (0.40 mL), *Symphytum officinale* (0.60 mL), *Mahonia aquifolium* (0.60 mL), *Echinacea purpurea* (0.20 mL), *Stellaria media* (0.80 mL), *Galium aparine* (0.80 mL), *Aloe vera* (0.60 mL), *Matricaria recutita* (0.60 mL), *Hypericum perforatum* (0.40 mL), *Calendula officinalis* (0.40 mL), and *Panax ginseng* (0.60 mL) were combined in a vessel. The extract combination was then made up to 100 mL by the addition of 5 ppm aqueous colloidal silver to provide a topically applicable composition.

Example 33

This is an example of a composition for applying to cuts.

Aqueous extracts of *Equisetum arvense* (0.60 mL), *Symphytum officinale* (0.80 mL), *Echinacea purpurea* (0.60 mL), *Stellaria media* (0.40 mL), *Aloe vera* (0.60 mL), *Matricaria recutita* (0.40 mL), *Hypericum perforatum* (0.40 mL), *Calendula officinalis* (0.80 mL), and *Panax ginseng* (0.80 mL) were combined in a vessel. The extract combination was then made up to 100 mL by the addition of 5 ppm aqueous colloidal silver to provide a topically applicable composition.

Example 34

This is an example of a composition for applying to Tinea pedis (Athlete's Foot).

Aqueous extracts of *Chelidonium majus* (0.20 mL), *Thuja occidentalis* (0.60 mL), *Echinacea purpurea* (0.40 mL), *Galium aparine* (0.40 mL), *Matricaria recutita* (0.40 mL), *Hypericum perforatum* (0.40 mL), and *Calendula officinalis* (0.80 mL) were combined in a vessel. The extract combination was then made up to 100 mL by the addition of 5 ppm aqueous colloidal silver to provide a topically applicable composition.

Example 35

This is an example of a composition for applying to sunburn.

Aqueous extracts of *Galium aparine* (0.60 mL) *Aloe vera* (0.80 mL), *Matricaria recutita* (0.60 mL), *Hypericum perforatum* (0.80 mL), *Calendula officinalis* (0.80 mL), and *Panax ginseng* (0.60 mL) were combined in a vessel. The extract combination was then made up to 100 mL by the addition of 5 ppm aqueous colloidal silver to provide a topically applicable composition.

Example 36

This is an example of a composition for applying to moles.

Aqueous extracts of *Chelidonium majus* (0.40 mL), *Thuja occidentalis* (0.80 mL), *Mahonia aquifolium* (0.20 mL), *Aloe vera* (0.20 mL), *Matricaria recutita* (0.20 mL), and *Calendula officinalis* (0.80 mL) were combined in a vessel. The extract combination was then made up to 100 mL by the addition of 5 ppm aqueous colloidal silver to provide a topically applicable composition.

Example 37

This is an example of a composition for applying to insect bites.

Aqueous extracts of *Arctium lappa* (0.60 mL), *Urtica dioica* (0.80 mL), *Echinacea purpurea* (0.80 mL), *Stellaria media* (0.60 mL), *Matricaria recutita* (0.40 mL), *Hypericum perforatum* (0.60 mL), and *Calendula officinalis* (0.60 mL) were combined in a vessel. The extract combination was then made up to 100 mL by the addition of 5 ppm aqueous colloidal silver to provide a topically applicable composition.

Example 38

This is an example of a composition for applying to Irritant diaper dermatitis.

Aqueous extracts of *Urtica dioica* (0.60 mL), *Symphytum officinale* (0.80 mL), *Echinacea purpurea* (0.60 mL), *Stellaria media* (0.60 mL), *Aloe vera* (0.80 mL), *Matricaria recutita* (0.80 mL), and *Calendula officinalis* (0.80 mL) were combined in a vessel. The extract combination was then made up to 100 mL by the addition of 5 ppm aqueous colloidal silver to provide a topically applicable composition.

Example 39

This is an example of a composition for use in the treatment of contact dermatitis related to incontinence.

Aqueous extracts of *Urtica dioica* (0.60 mL), *Symphytum officinale* (0.80 mL), *Mahonia aquifolium* (0.40 mL), *Echinacea purpurea* (0.80 mL), *Stellaria media* (0.60 mL), *Aloe vera* (0.60 mL), *Matricaria recutita* (0.80 mL), *Hypericum perforatum* (0.60 mL), *Calendula officinalis* (0.60 mL), and *Panax ginseng* (0.80 mL) were combined in a vessel. The extract combination was then made up to 100 mL by the addition of 5 ppm aqueous colloidal silver to provide a topically applicable composition.

Example 40

This is an example of a composition for applying to the skin of household pets.

Aqueous extracts of *Rumex crispus* (0.60 mL), *Arctium lappa* (0.60 mL), *Trzfolium pratense* (0.60 mL), *Symphytum officinale* (0.40 mL), *Echinacea purpurea* (0.60 mL), *Stellaria media* (0.40 mL), *Hypericum perforatum* (0.40 mL), *Calendula officinalis* (0.40 mL), and *Panax ginseng* (0.40 mL) were combined in a vessel. The extract combination was then made up to 100 mL by the addition of 5 ppm aqueous colloidal silver to provide a topically applicable composition.

Example 41

This is an example of a composition suitable to be provided in combination with a form of application, such as a porous sheet impregnated with the composition.

Aqueous extracts of *Urtica dioica* (0.60 mL), *Symphytum officinale* (0.80 mL), *Echinacea purpurea* (0.60 mL), *Stellaria media* (0.60 mL), *Aloe vera* (0.80 mL), *Matricaria recutita* (0.80 mL), and *Calendula officinalis* (0.80 mL), were combined in a vessel. The extract combination was then made up to 100 mL by the addition of 5 ppm aqueous colloidal silver to provide a composition. A porous sheet was treated with the resulting composition to provide a porous sheet impregnated with the composition (a "wet wipe").

Example 42

This is an example of a composition suitable to be provided in combination with a form of application, such as a porous sheet impregnated with the composition, wherein the composition is suitable for use with household pets.

Aqueous extracts of *Rumex crispus* (0.60 mL), *Arctium lappa* (0.60 mL), *Trifolium pratense* (0.60 mL), *Symphytum officinale* (0.40 mL), *Echinacea purpurea* (0.60 mL), *Stellaria media* (0.40 mL), *Matricaria recutita* (0.40 mL), and *Calendula officinalis* (0.40 mL) were combined in a vessel. The extract combination was then made up to 100 mL by the addition of 5 ppm aqueous colloidal silver to provide a composition. A porous sheet was treated with the resulting composition to provide a porous sheet impregnated with the composition (a "wet wipe").

DESCRIPTION OF EMBODIMENTS WITH REFERENCE TO THE FIGURES

FIG. 1 shows a subject 100 with an area of unbroken skin 110. A localised area of skin 120 presents with an open wound 122. This picture of subject 100 was taken at 15:00 on Day 0 of a test period, prior to application of any composition described herein.

Figure 2:
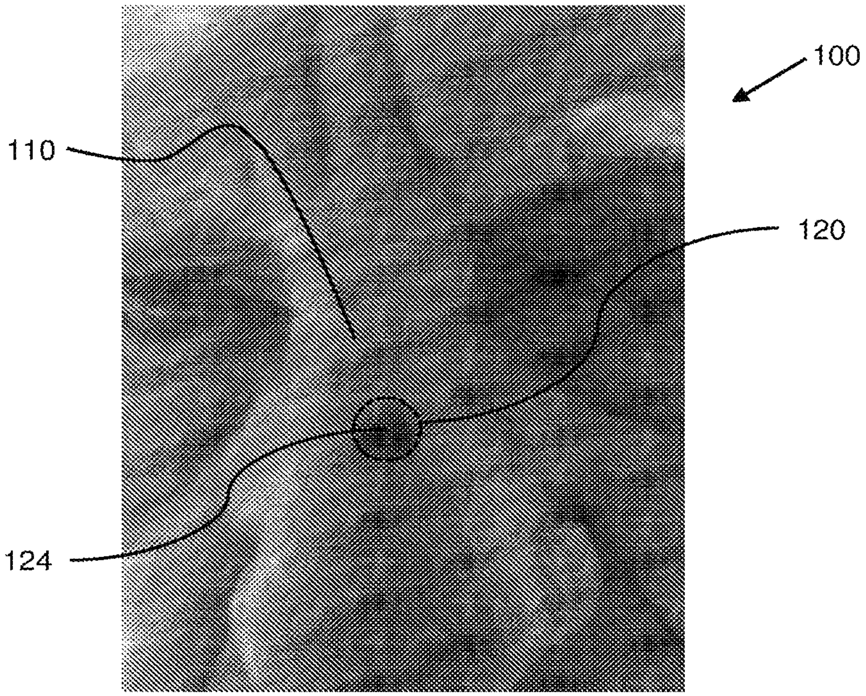
FIGS. 2, 3 and 4 show the variation in appearance of the wound of FIG. 1 over time after application of a composition of the present invention to the affected area.

A composition consisting of aqueous extracts of *Equisetum arvense, Symphytum officinale, Echinacea purpurea, Stellaria media, Aloe vera, Matricaria recutita, Hypericum peiforatum, Calendula officinalis,* and *Panax ginseng* in a ratio of 3:4:3:2:3:2:2:4:4 (w/w) in 5 ppm aqueous colloidal silver was prepared (corresponding to Example 33). The area of skin 120 containing the wound was selected, and the composition topically applied to the selected area. Said composition was regularly applied to the area 120 through a test period of 8 days. FIG. 2 is a picture of subject 100 taken at 10:22 on Day 3 of the test period. The open wound 102 in area 120 has scabbed to provide a scabbed wound 124.

Figure 3:
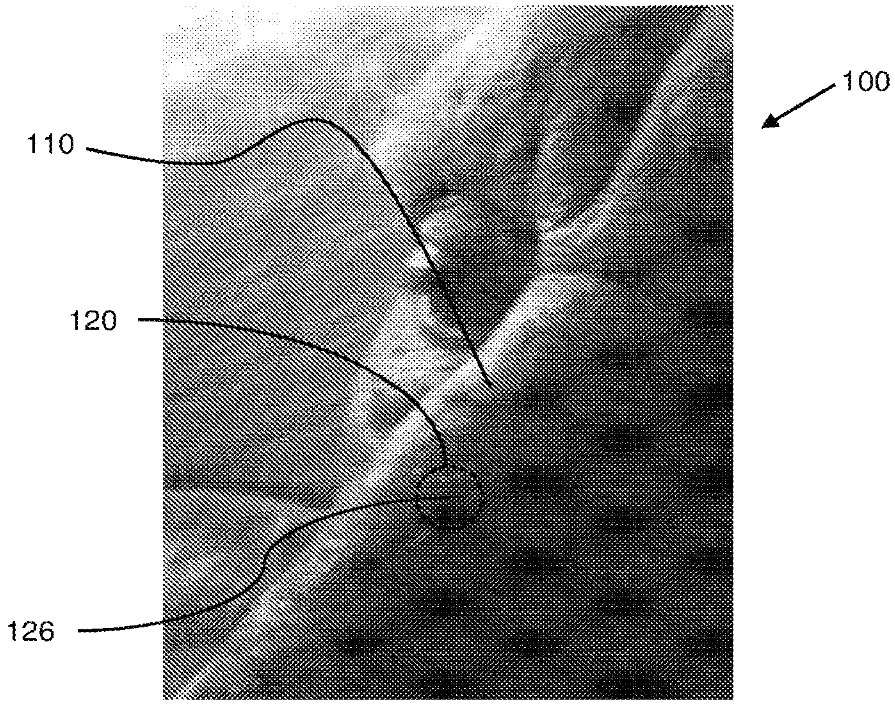

FIG. 3 is a picture of the subject 100 taken at 16:26 on Day 6 of the test period, showing a decrease in the size of scabbed wound 124 in area 120 to provide scabbed wound 126.

Figure 4:
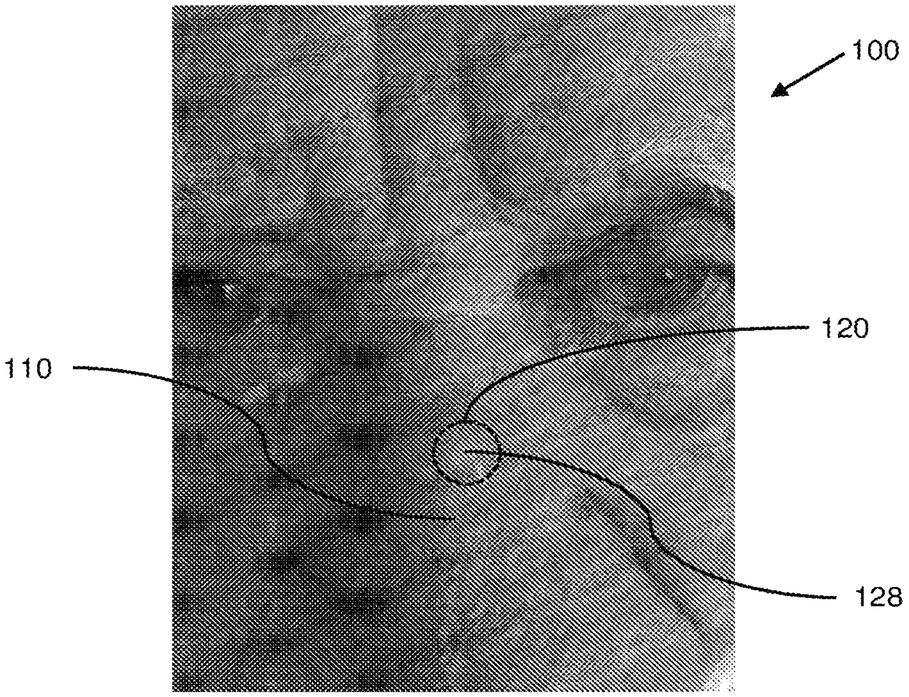

FIG. 4 is a picture of the subject 100 representing the appearance of Subject 100 on Day 8 of the test period. Scabbed wound 124 in area 120 has healed completely to provide new skin 128. New skin 128 in the area of skin 120 on Day 8 resembles the unbroken 110. Thus, FIGS. 1 to 4 demonstrate that regular application of a composition of the present invention to an open wound may result in an increased rate of healing of the wound.

In another example, a subject 200 presented with a nevi (mole) in a localised area of skin 220. The nevi was roughly circular in shape, had a darker pigmentation compared with the surrounding normal skin tone, and protruded from the surface of the skin. A composition consisting of aqueous extracts of *Chelidonium inajus, Thuja occidentalis, Mahonia aquzfolium, Aloe vera, Matricaria recutita,* and *Calendula officinalis* in a ratio of 2:4:1:1:1:4 (w/w) in 5 ppm aqueous colloidal silver was prepared (corresponding to Example 36). The area of skin 220 containing the nevi was selected, and the composition topically applied to the selected area. Said composition was regularly applied to the selected area through a test period of 95 days.

Figure 5:
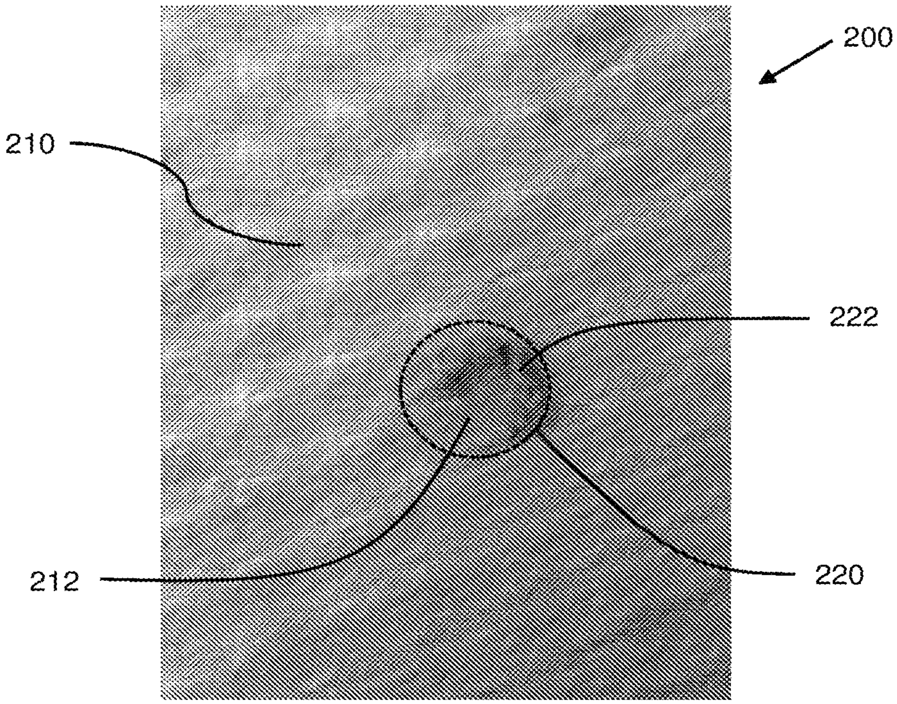
FIGS. 5 and 6 show the variation in appearance of a nevi over a period of time after application of a composition of the present invention to the affected area.

FIG. 5 is a picture of subject 200 taken on Day 80 of the test period. Subject 200 has an area of normal skin tone 210. The localised area of the skin 220 presents with a portion of darker pigmentation 222 compared to the normal skin tone 210. The darker pigmentation 222 also protrudes from the surrounding normal skin 210. The size of the nevi, the pigmentation of the area 220, and the protrusion of the nevi from the skin are reduced compared with the appearance of the nevi prior to application of the composition. In particular, localised area of skin 220 now contains normal skin tone 212, whereas on Day 0 this area was part of the nevi.

Figure 6:
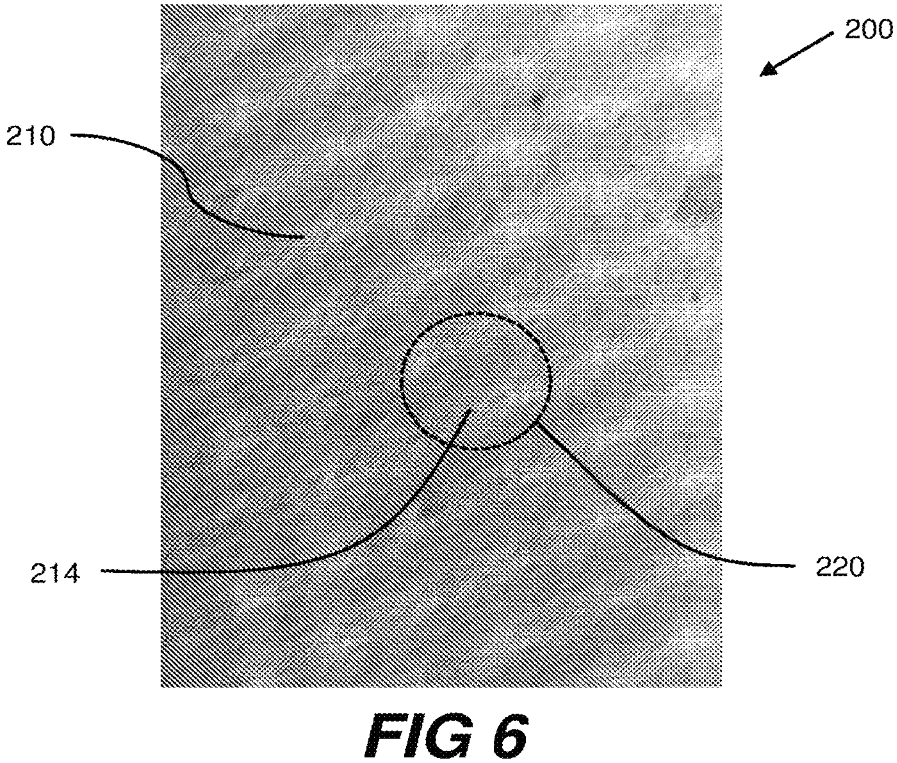

FIG. 6 is a picture representing the appearance of Subject 200 on Day 95 of the test period. The pigmentation of the skin 222 has substantially decreased; the pigmentation of the skin 222 in the area of the body 220 now resembles the normal skin tone 210, and area of skin 220 now contains only skin of normal skin tone 214. Further, there is now no protrusion from the body. Thus, FIGS. 5 and 6 demonstrate that regular application of a composition of the present invention to a nevi may result in a reduction in the pigmentation and physical protrusion of the nevi.

Figure 7:
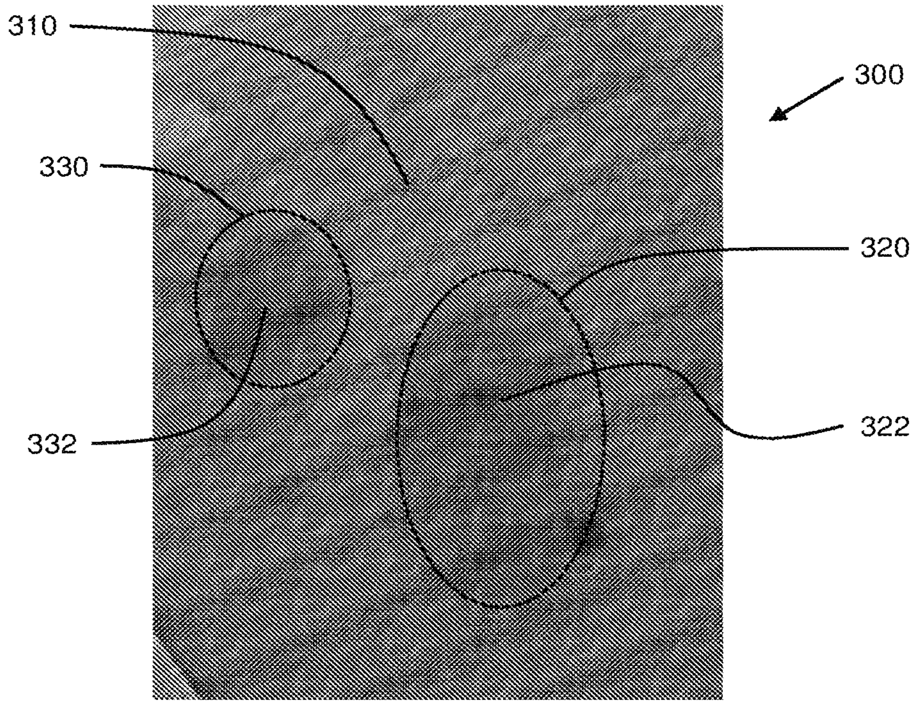
FIG. 7 shows a subject presenting with two insect bites on the skin.

FIG. 7 shows a subject 300 with a normal skin tone 310. Localised areas of skin 320 and 330 present with recently inflicted mosquito bites, resulting in reddened and raised skin 322 and 332. This picture of subject 300 was taken prior to topical application of any composition described herein.

A composition consisting of aqueous extracts of *Arctium lappa, Urtica dioica, Echinacea purpurea, Stellaria media, Matricaria recutita, Hypericum perforatum,* and *Calendula officinalis,* in a ratio of 3:4:4:3:2:3:3 (w/w) in 5 ppm aqueous colloidal silver was prepared (corresponding to Example 37). The areas of skin 320 and 330 presenting with insect bites were selected, and the composition topically applied to the selected areas. Said composition was regularly applied (three times-daily) to the areas 320 and 330 through a test period of 24 hours.

Figure 8:
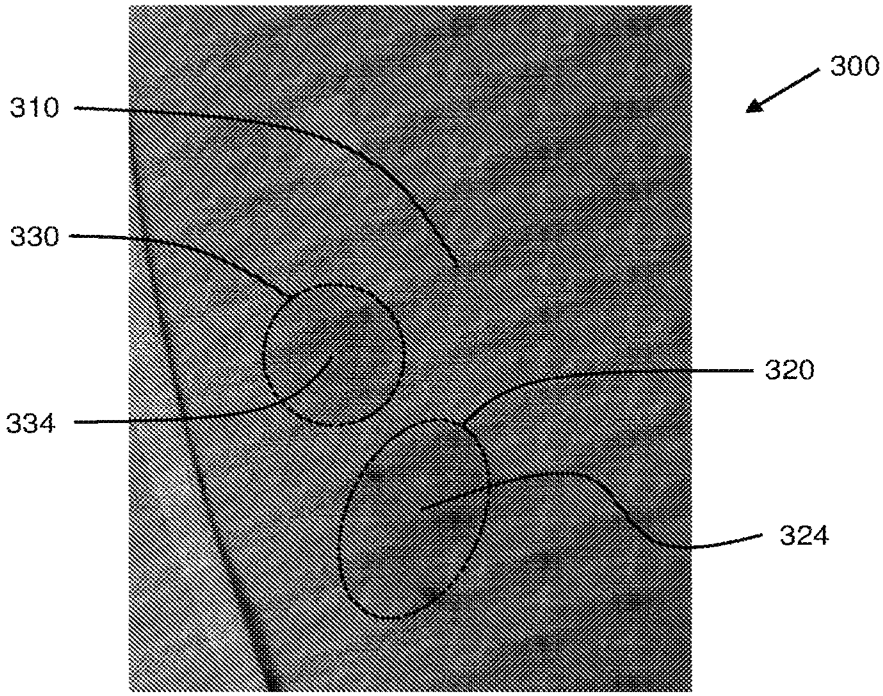
FIGS. 8 and 9 show the variation in appearance of the insect bites of FIG. 7 over time after application of a composition of the present invention to the affected area.

FIG. 8 is a picture of the subject 300 taken after 6 hours of the test period. Reddened and raised skin 324 and 334 is decreased in size compared with reddened and raised skin 322 and 332. Reddened and raised skin 324 and 334 is of a skin tone more similar to normal skin tone 310 than reddened and raised skin 322 and 332.

Figure 9:
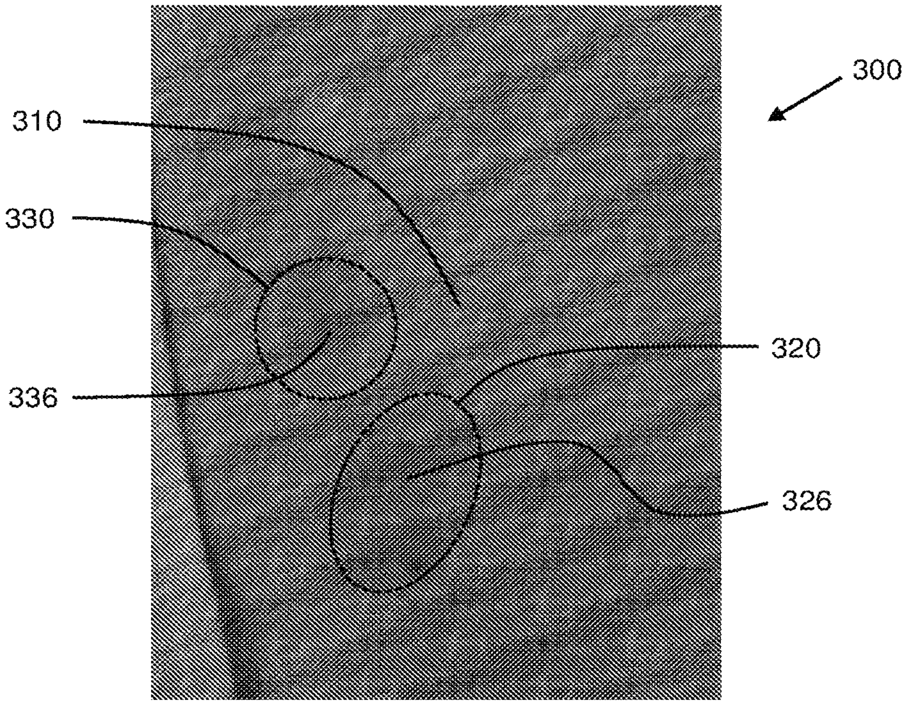

FIG. 9 is a picture of the subject 300 taken after 24 hours of the test period. Reddened and raised skin 326 and 336 is yet further decreased in size compared with reddened and raised skin 324 and 334. Reddened and raised skin 326 and 336 is of a skin tone even more similar to normal skin tone 310 than reddened and raised skin 324 and 334. Subject 300 also reported a perceived reduction in the itching sensation provided by the mosquito bite after application of the composition.

Thus, FIGS. 7 to 9 demonstrate that regular application of a composition of the present invention to an insect bite, in particular a mosquito bite, may result in a reduction in the size, reddening and itchiness of an insect bite.

Figure 10:
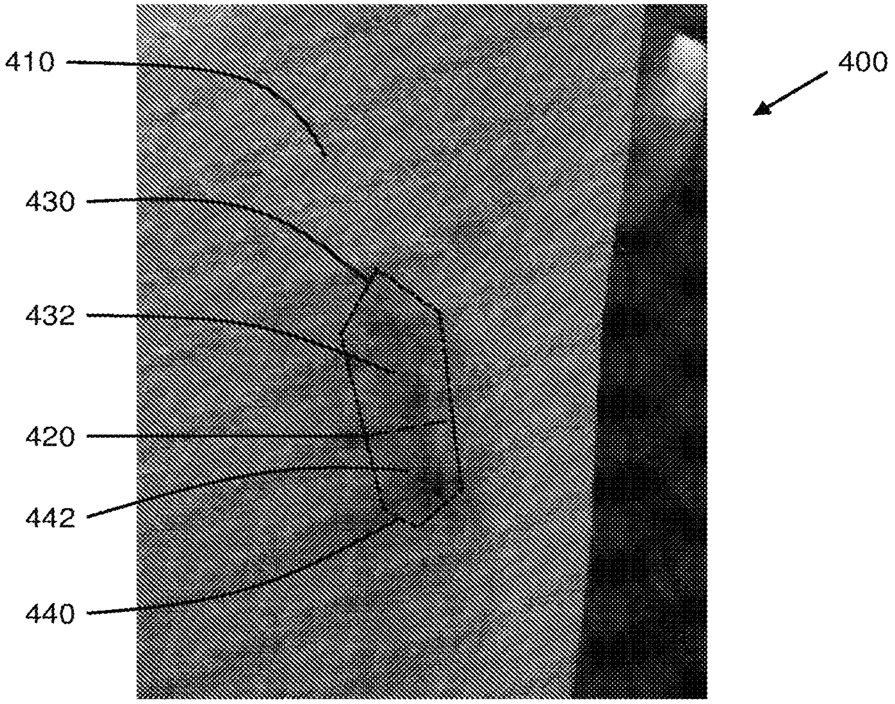
FIG. 10 shows a subject presenting with an open wound.

FIG. 10 shows a subject 400 with unbroken skin 410. Localised area of skin 420 contains a recently inflicted open wound. Localised area of skin 420 contains two smaller areas 430 and 440. Area 430 contains a portion of open wound 432; area 440 contains a portion of scabbed wound 442. This picture of subject 400 was taken at 09:30 on Day 0 of a test period prior to topical application of any composition described herein.

A composition consisting of aqueous extracts of *Equisetum arvense, Symphytuin officinale, Echinacea purpurea, Stellaria media, Aloe vera, Matricaria recutita, Hypericum perforatum, Calendula officinalis,* and *Panax ginseng* in a ratio of 3:4:3:2:3:2:2:4:4 (w/w) in 5 ppm aqueous colloidal silver was prepared (corresponding to Example 33). The area of skin 420 containing the wound was selected, and the composition topically applied to the selected area. Said composition was regularly applied to the areas 420 for the first 5 days of a test period of 10 days.

Figure 11:
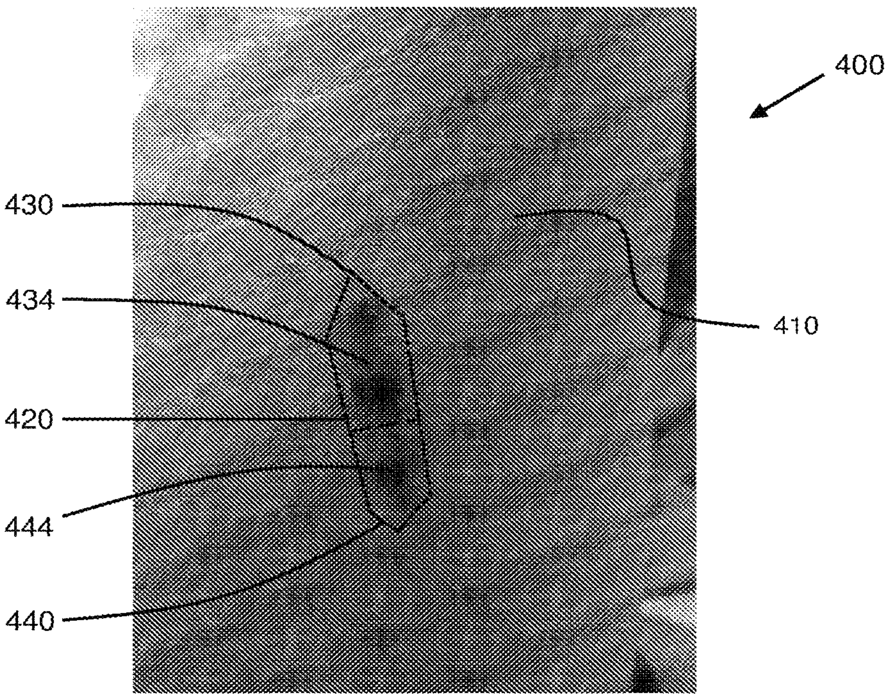
FIGS. 11 and 12 show the variation in appearance of the wound of FIG. 10 over time after application of a composition of the present invention to the affected area.

FIG. 11 is a picture of the subject 400 taken at 10:12 on Day 3 of the test period. The portion of open wound 432 in area 430 has scabbed to provide portion of scabbed wound 434 in area 430. The portion of scabbed wound 442 in area 440 has reduced in size to provide portion of scabbed wound 444 in area 440. The inflammation surrounding portions of wound 434 and 444 in area 420 is reduced compared with that shown in FIG. 10.

Figure 12:
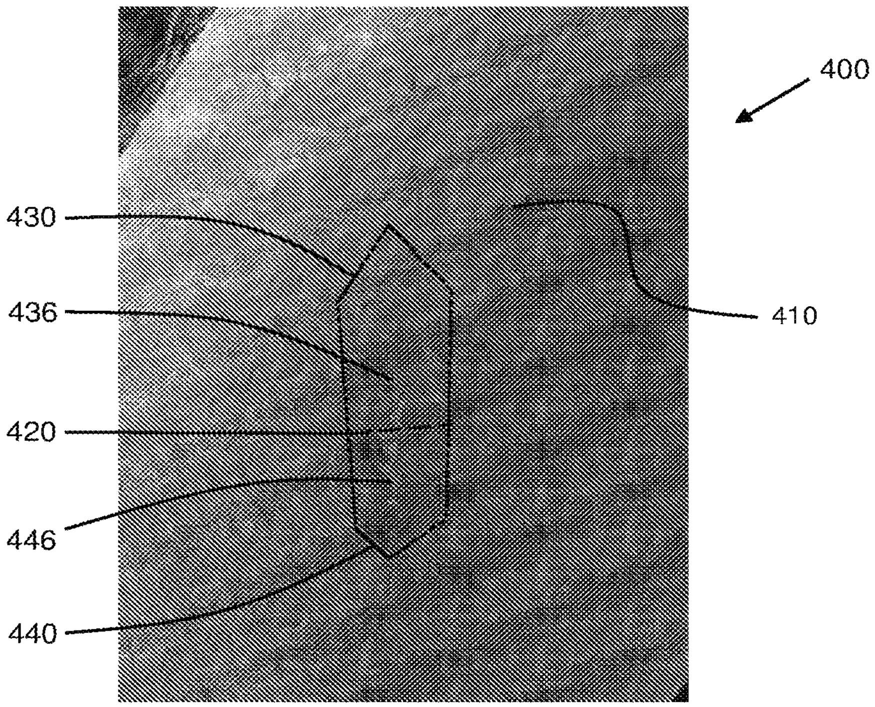

FIG. 12 is a picture representing the appearance of Subject 400 at 11:17 on Day 10 of the test period. The portion of scabbed wound 434 in area 430 has healed to provide new skin 436 in area 430. The portion of scabbed wound 444 in area 440 has healed to provide new skin 446 in area 440. A wound of this magnitude inflicted on subject 400 would not usually be expected to heal within 10 days. Thus, FIGS. 10 to 12 demonstrate that regular application of a composition of the present invention to a wound may result in an increased rate of healing of the wound.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

The invention claimed is:

1. A cosmetic composition for topical application on skin afflicted with a dermatological condition and/or cosmetic skin condition, comprising an aqueous solution, and dispersed within the aqueous solution:

i) an elemental silver as a colloidal suspension, the elemental silver being present in an amount of from $1\times10^{-5}$% to $1\times10^{-2}$% by weight/volume of the aqueous solution, ii) a plant extract mixture in an amount of from 0.1% to 10% by weight/volume (w/v) of the aqueous solution, wherein the plant extract mixture comprises 6 to 17 extracts from plants selected from *Echinacea purpurea, Stellaria media, Aloe vera, Matricaria recutita, Hypericum perforatum, Calendula officinalis, Equisetum arvense, Symphytum officinale, Panax ginseng, Rumex crispus, Arctium lappa, Trifolium pratense, Chelidonium majus, Thuja occidentalis, Urtica dioica, Mahonia aquifolium,* and *Galium aparine,* wherein at least two of the plants are *Calendula officinalis* and *Matricaria recutita,* wherein the plant extract mixture and colloidal suspension are combined in a ratio of 1:20 to 1:4 (w/v) plant extract to colloidal suspension of silver, and iii) water as the remainder of the aqueous solution in an amount up to 100% by weight/volume, wherein the cosmetic composition comprising the aqueous solution is impregnated on a porous sheet for application to the dermatological condition and/or cosmetic skin condition, and wherein the cosmetic composition alleviates at least one of pain, itching, burning, reddening of the skin, dry skin, and/or pigmentation of the skin.

2. A composition according to claim 1, wherein the plant extract mixture is an extract in an extractant selected from $C_1$-$C_4$ alkanol, acetic acid, glycerine, propylene glycol, honey, water, and mixtures thereof.

3. A composition according to claim 2, wherein the plant extract mixture is in a solution consisting of aqueous ethanol.

4. A composition according to claim 2, wherein the plant extract mixture is an extract of plant material in a ratio of from 1:1 to 1:12 weight/volume of plant material to extractant.

5. A composition according to claim 2, wherein the extractant is removed, and the composition is a maceration comprising chopped plant material in cold water consisting of the selected plant components.

6. A composition according to claim 1, wherein at least four of the plants are *Calendula officinalis, Matricaria recutita, Echinacea purpurea,* and *Hypericum perforatum.*

7. A composition according to claim 1, wherein at least five of the plants are *Calendula officinalis, Matricaria recutita, Stellaria media, Symphytum officinale,* and *Aloe vera.*

8. A composition according to claim 1, wherein at least three of the plants are *Calendula officinalis, Matricaria recutita,* and *Panax ginseng.*

9. A composition according to claim 1, wherein at least four of the plants are *Calendula officinalis, Matricaria recutita, Urtica dioica,* and *Articum lappa.*

10. A composition according to claim 1, wherein at least four of the plants are *Calendula officinalis, Matricaria recutita, Galium aparine,* and *Mahonia equifolium.*

11. A composition according to claim 1, wherein at least four of the plants are *Calendula officinalis, Matricaria recutita, Thuja occidentalis,* and *Chelidonium majus.*

12. A composition according to claim 1, wherein at least four of the plants are *Calendula officinalis, Matricaria recutita, Trifolium pratense,* and *Rumex crispus.*

13. A composition according to claim 1, wherein at least three of the plants are *Calendula officinalis, Matricaria recutita,* and *Equisetum arvense.*

14. A composition according to claim 1, wherein the plant extract mixture and colloidal suspension are combined in a ratio of 1:15 to 1:6 (w/v) plant extract to colloidal suspension of silver.

15. A composition according to claim 1, wherein the plant extract mixture and colloidal suspension are combined in a ratio of 1:12 to 1:8 (w/v) plant extract to colloidal suspension of silver.

* * * * *